US007250280B2

(12) United States Patent
Jensen et al.

(10) Patent No.: US 7,250,280 B2
(45) Date of Patent: *Jul. 31, 2007

(54) METHOD OF IMPROVING THE PRODUCTION OF BIOMASS OR A DESIRED PRODUCT FROM A CELL

(75) Inventors: Peter Ruhdal Jensen, Søgårdsvej 19, Gentofte (DK) DK-2820; Jacky Leendert Snoep, Amsterdam (NL); Hans Victor Westerhoff, Amsterdam (NL)

(73) Assignee: Peter Ruhdal Jensen, Gentofte (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/075,398

(22) Filed: Mar. 7, 2005

(65) Prior Publication Data
US 2006/0094078 A1   May 4, 2006

Related U.S. Application Data

(60) Continuation of application No. 10/310,630, filed on Dec. 5, 2002, now abandoned, which is a division of application No. 09/254,504, filed on Aug. 4, 1999, now Pat. No. 6,511,836.

(51) Int. Cl.
*C12N 9/10* (2006.01)
*C12N 1/20* (2006.01)
*C12N 15/00* (2006.01)
*C12Q 1/48* (2006.01)

(52) U.S. Cl. ............... 435/193; 435/4; 435/15; 435/252.3; 435/320.1; 435/252.33; 435/252.5; 435/254.1; 435/255.1; 536/23.2; 536/23.7

(58) Field of Classification Search ............... 435/193, 435/15, 252.3, 320.1, 252.33, 252.5, 254.1, 435/255.1, 4; 536/23.2, 23.7
See application file for complete search history.

(56) References Cited

U.S. PATENT DOCUMENTS 6,511,836 B1 * 1/2003 Jensen et al. ............... 435/193

FOREIGN PATENT DOCUMENTS

| EP | 0472 286 | 2/1992 |
|---|---|---|
| EP | 0 645 094 | 3/1995 |
| WO | WO 87/03006 | 5/1987 |
| WO | WO 94/00493 | 1/1994 |

OTHER PUBLICATIONS

Abrahams et al., (1994) *Nature*, 370:621-628.
Ali et al., (1993) The 43-Kilodalton N-Terminal Fragment of the DNA Gyrase B Protein Hydrolyzes ATP and Binds Coumarin Drugs.
Biswass et al., (1999) *Biochemistry*, 38: 10919-10928.
European Search Report, Dec. 4, 1997.
Flaherty et al., (1990) *Nature*, 346:623-628.
Israelsen et al., (1995) *Applied and Environmental Microbiology*, 61:2540-2547.
Maxwell A. (1993) *Proc natl Acad Sci USA*, 90:11232-11236.
Moritani et al., (May 20, 1996) *B.B.A.*, 1274:67-72.
Nakatogawa et al., (2000) *J. Biol. Chem.*, 275:33209-33212.
Nakayama et al., (1984) *J. Biol. Chem.*, 259:88-96.
Nelson N. (1989) *J. of Bioenergetics and Biomembranes*, 21:553-571.
Otterson et al., (1994) *EMBO Journal*, 13:1216-1225.
Santana et al., (1994) *Journal of Bacteriology*, 176:6802-6811.
Sarin et al., (2001) *J. Biol. Chem.*, 276:44590-44597.
Senior AE (1990) *Annu Rev Biophys Biophys Chem*, 19:7-41 Review.
Serrano R. (1984) *Current Topics in Cellular Regulation*, 23:87-126.
Shibata et al., (1992) *Journal of Bacteriology*, 19:6117-6124.
Stark M. (1987) *Gene*, 51:255-267.
Stevens et al., (1997) *Annu Rev Cell Dev Biol*, 13:779-808 Review.
Takeda, et al., (1985) *The Journal of Biology Chemistry*, 29:15458-15465.
von Meyenburg et al. (1984) *EMBO Journal*, 3:1791-1797.

* cited by examiner

*Primary Examiner*—Tekchand Saidha
(74) *Attorney, Agent, or Firm*—Darby & Darby

(57) ABSTRACT

The production of biomass or a desired product from a cell can be improved by inducing conversion of ATP to ADP without primary effects on other cellular metabolites or functions which is achieved by expressing an uncoupled ATPase activity in the cell and incubating the cell with a suitable substrate to produce the biomass or product. This is conveniently done by expressing in the cell the soluble part ($F_1$) of the membrane bound ($F_0F_1$ type) $H^+$ ATPase or a portion of $F_1$ exhibiting ATPase activity. The organism from which the $F_1$ ATPase or portions thereof is derived, or in which the $F_1$ ATPase or portions thereof is expressed, may be selected from prokaryotes and eukaryotes. In particular the DNA encoding $F_1$ or a portion thereof may be derived from bacteria and eukaryotic microorganisms such as yeasts, other fungi and cell lines of higher organisms and be selected from the group consisting of the gene encoding the $F_1$ subunit $\beta$ or a portion thereof and various combinations of the gene or portion with the genes encoding the other $F_1$ subunits or portions thereof. The method can be used i.a. for optimizing the formation of biomass or a desired product by a cell by expressing different levels of uncoupled ATPase activity in the cell, incubating the cell on a suitable substrate, measuring the conversion rate of substrate into biomass or the desired product at each level of ATPase expression, and choosing level of ATPase expression at which the conversion rate is optimized.

15 Claims, 4 Drawing Sheets

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
    (A) LENGTH: 4815 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Lactococcus lactis subsp. cremoris
    (B) STRAIN: MG1363

(ix) FEATURE:
    (A) NAME/KEY: CDS
    (B) LOCATION:26..550
    (D) OTHER INFORMATION:/codon_start= 26
      /product= "ATPase subunit"
      /gene= "atpH"
      /standard_name= "delta subunit of the F1 portion
      of the F0F1 ATPase"
      /label= delta-subunit (ix) FEATURE:
    (A) NAME/KEY: CDS
    (B) LOCATION:742..2241
    (D) OTHER INFORMATION:/codon_start= 742
      /product= "ATPase subunit"
      /gene= "atpA"
      /standard_name= "alpha subunit of the F1 portion
      of the F0F1 ATPase"
      /label= alpha-subunit (ix) FEATURE:
    (A) NAME/KEY: CDS
    (B) LOCATION:2260..3126
    (D) OTHER INFORMATION:/codon_start= 2260
      /product= "ATPase subunit"
      /gene= "atpG"
      /standard_name= "gamma subunit of the F1 portion
      of the F0F1 ATPase"
      /label= gamma-subunit (ix) FEATURE:
    (A) NAME/KEY: CDS
    (B) LOCATION:3301..4707
    (D) OTHER INFORMATION:/codon_start= 3301
      /product= "ATPase subunit"
      /gene= "atpD"
      /standard_name= "beta subunit of the F1 portion of
      the F0F1 ATPase"
      /label= beta-subunit (xi) SEQUENCE DESCRIPTION: SEQ ID NO: 1:

```
TATCTCGCTA AGTTAGGAGA ATAAG ATG ACA AAA GTA AAT TCA CAA AAA TAC        52
                           Met Thr Lys Val Asn Ser Gln Lys Tyr
                            1               5

AGT AAA GCT TTA CTT GAG GTC GCC CGA GAA AAA GGA CAA CTT GAA GCA       100
Ser Lys Ala Leu Leu Glu Val Ala Arg Glu Lys Gly Gln Leu Glu Ala
 10              15                  20                  25

ATT CTT ACT GAA GTT AGC GAA ATG ATT CAG CTT TTC AAA GAA AAT AAC       148
Ile Leu Thr Glu Val Ser Glu Met Ile Gln Leu Phe Lys Glu Asn Asn
         30                  35                  40
```

```
TTA GGT GCT TTT TTA GCA AAT GAA GTT TAT TCA TTC TCT GCT AAA TCT        196
Leu Gly Ala Phe Leu Ala Asn Glu Val Tyr Ser Phe Ser Ala Lys Ser
            45                  50                  55

GAA TTG ATT GAT ACT TTG CTT CAA ACT TCA TCA GAA GTG ATG TCA AAT        244
Glu Leu Ile Asp Thr Leu Leu Gln Thr Ser Ser Glu Val Met Ser Asn
        60                  65                  70

TTC CTG AAT ACT ATT CGT TCT AAT GGA CGT CTA GCT GAC CTC GGA GAA        292
Phe Leu Asn Thr Ile Arg Ser Asn Gly Arg Leu Ala Asp Leu Gly Glu
    75                  80                  85

ATA CTT GAA GAA ACT AAA AAT GCA GCA GAT GAC ATG TTC AAA ATT GCT        340
Ile Leu Glu Glu Thr Lys Asn Ala Ala Asp Asp Met Phe Lys Ile Ala
90                  95                  100                 105

GAC GTT GAA GTT GTT TCA AGT ATT GCA TTG TCA GAA GCT CAA ATT GAA        388
Asp Val Glu Val Val Ser Ser Ile Ala Leu Ser Glu Ala Gln Ile Glu
                110                 115                 120

AAA TTT AAA GCA ATG GCT AAA TCA AAA TTT GAT TTA AAC GAA GTA ACA        436
Lys Phe Lys Ala Met Ala Lys Ser Lys Phe Asp Leu Asn Glu Val Thr
            125                 130                 135

GTA ATT AAT ACA GTC AAT GAA AAA ATT CTC GGA GGA TTC ATT GTG AAC        484
Val Ile Asn Thr Val Asn Glu Lys Ile Leu Gly Gly Phe Ile Val Asn
        140                 145                 150

TCT CGT GGA AAA ATT ATT GAC GCC TCA TTA AAA ACA CAA TTG GCT AAA        532
Ser Arg Gly Lys Ile Ile Asp Ala Ser Leu Lys Thr Gln Leu Ala Lys
    155                 160                 165

ATC GCC GCT GAA ATC CTC TAATCAGGAT AGAAAAATTT TCTTCCTTTG              580
Ile Ala Ala Glu Ile Leu
170                 175

TTAAAAACTT AGTGGAGAAT TTTTCAAACT CAAACTGTTA AACTTTTGAA AACATGCAAA      640

GGTAATTTTA AAACTTGCTT ATTCATGCTC AAAAAGTATA ACTGCAGTTT AAAGCTAAAT      700

AGCCTTGAAC TAGTAAAAAA TTTCTAGAAG GGAGCATATT T TTG GCA ATT AAA         753
                                              Leu Ala Ile Lys
                                               1

GCT AAT GAA ATC AGC TCA CTG ATT AAA AAA CAA ATT GAA AAT TTC ACA        801
Ala Asn Glu Ile Ser Ser Leu Ile Lys Lys Gln Ile Glu Asn Phe Thr
 5                  10                  15                  20

CCA GAT TTT GAA GTT GCT GAA ACT GGT GTC GTT ACC TAT GTT GGT GAT        849
Pro Asp Phe Glu Val Ala Glu Thr Gly Val Val Thr Tyr Val Gly Asp
            25                  30                  35

GGT ATC GCG CGT GCC TAT GGC CTT GAA AAT GCG ATG AGC GGT GAG CTT        897
Gly Ile Ala Arg Ala Tyr Gly Leu Glu Asn Ala Met Ser Gly Glu Leu
        40                  45                  50

GTT GAG TTT TCA AAT GGT ATA CTT GGT ATG GCG CAA AAC TTG GAT GCT        945
Val Glu Phe Ser Asn Gly Ile Leu Gly Met Ala Gln Asn Leu Asp Ala
    55                  60                  65

ACA GAC GTT GGT ATT ATC GTA CTT GGT GAT TTC CTC TCA ATT CGT GAA        993
Thr Asp Val Gly Ile Ile Val Leu Gly Asp Phe Leu Ser Ile Arg Glu
70                  75                  80

GGT GAC ACT GTT AAA CGT ACA GGT AAA ATC ATG GAA ATC CAA GTT GGT       1041
Gly Asp Thr Val Lys Arg Thr Gly Lys Ile Met Glu Ile Gln Val Gly
            85                  90                  95                  100

GAA GAA CTC ATC GGA CGT GTT GTA AAC CCA CTT GGA CAA CCC GTT GAT       1089
Glu Glu Leu Ile Gly Arg Val Val Asn Pro Leu Gly Gln Pro Val Asp
                    105                 110                 115

GGA CTT GGA GAA CTT AAT ACA GGT AAA ACT CGT CCA GTT GAA GCA AAA       1137
Gly Leu Gly Glu Leu Asn Thr Gly Lys Thr Arg Pro Val Glu Ala Lys
                120                 125                 130

GCT CCT GGT GTT ATG CAA CGT AAA TCA GTC TCT GAG CCA TTA CAA ACT       1185
Ala Pro Gly Val Met Gln Arg Lys Ser Val Ser Glu Pro Leu Gln Thr
```

```
                    135             140             145
GGT CTT AAA GCG ATT GAT GCC CTC GTT CCA ATT GGA CGT GGA CAA CGT       1233
Gly Leu Lys Ala Ile Asp Ala Leu Val Pro Ile Gly Arg Gly Gln Arg
    150             155             160

GAA TTA ATT ATC GGA GAC CGT CAA ACT GGT AAA ACT TCA GTC GCT ATT       1281
Glu Leu Ile Ile Gly Asp Arg Gln Thr Gly Lys Thr Ser Val Ala Ile
165             170             175             180

GAT GCA ATC TTG AAC CAA AAA GGT CAA GAT ATG ATT TGT ATC TAT GTT       1329
Asp Ala Ile Leu Asn Gln Lys Gly Gln Asp Met Ile Cys Ile Tyr Val
                185             190             195

GCG ATT GGA CAA AAA GAG TCA ACA GTT CGT ACA CAA GTT GAA ACG CTC       1377
Ala Ile Gly Gln Lys Glu Ser Thr Val Arg Thr Gln Val Glu Thr Leu
            200             205             210

CGT AAA CTC GGT GCG ATG GAT TAT ACA ATC GTC GTA ACT GCG TCA GCT       1425
Arg Lys Leu Gly Ala Met Asp Tyr Thr Ile Val Val Thr Ala Ser Ala
        215             220             225

TCT CAA CCT TCT CCA CTC CTT TAC ATC GCT CCT TAC GCT GGA GCT GCA       1473
Ser Gln Pro Ser Pro Leu Leu Tyr Ile Ala Pro Tyr Ala Gly Ala Ala
230             235             240

ATG GGT GAA GAA TTT ATG TAT AAC GGT AAA CAT GTC TTG GTT GTT TAT       1521
Met Gly Glu Glu Phe Met Tyr Asn Gly Lys His Val Leu Val Val Tyr
245             250             255             260

GAT GAT TTA TCT AAA CAA GCG GTC GCT TAC CGT GAA CTT TCT CTC TTG       1569
Asp Asp Leu Ser Lys Gln Ala Val Ala Tyr Arg Glu Leu Ser Leu Leu
                265             270             275

CTC CGT CGT CCA CCA GGT CGT GAA GCA TAC CCA GGT GAC GTT TTC TAC       1617
Leu Arg Arg Pro Pro Gly Arg Glu Ala Tyr Pro Gly Asp Val Phe Tyr
            280             285             290

TTG CAC TCA CGT CTT TTG GAA CGT GCT GCT AAA TTG TCT GAT GAT CTT       1665
Leu His Ser Arg Leu Leu Glu Arg Ala Ala Lys Leu Ser Asp Asp Leu
        295             300             305

GGT GGT GGA TCA ATG ACG GCT TTG CCA TTC ATT GAA ACA CAA GCA GGT       1713
Gly Gly Gly Ser Met Thr Ala Leu Pro Phe Ile Glu Thr Gln Ala Gly
310             315             320

GAT ATC TCA GCT TAT ATT CCA ACA AAC GTT ATC TCT ATT ACC GAC GGT       1761
Asp Ile Ser Ala Tyr Ile Pro Thr Asn Val Ile Ser Ile Thr Asp Gly
325             330             335             340

CAA ATT TTC CTT GAA AAT GAC TTG TTC TAT TCA GGT GTA CGT CCT GCC       1809
Gln Ile Phe Leu Glu Asn Asp Leu Phe Tyr Ser Gly Val Arg Pro Ala
                345             350             355

ATT GAT GCT GGT TCA TCA GTA TCA CGT GTT GGT GGT GCC GCA CAA ATC       1857
Ile Asp Ala Gly Ser Ser Val Ser Arg Val Gly Gly Ala Ala Gln Ile
            360             365             370

AAA GCC ATG AAG AAA GTA GCT GGT ACT TTG CGT CTT GAC CTT GCG TCG       1905
Lys Ala Met Lys Lys Val Ala Gly Thr Leu Arg Leu Asp Leu Ala Ser
        375             380             385

TTC CGT GAA CTT GAA GCC TTT ACA CAA TTT GGT TCT GAC CTT GAT GAA       1953
Phe Arg Glu Leu Glu Ala Phe Thr Gln Phe Gly Ser Asp Leu Asp Glu
390             395             400

GCG ACT CAA GCA AAA TTG AAT CGT GGT CGT CGT ACC GTT GAA GTC TTG       2001
Ala Thr Gln Ala Lys Leu Asn Arg Gly Arg Arg Thr Val Glu Val Leu
405             410             415             420

AAA CAA CCA TTG CAC AAA CCA TTG GCT GTT GAA AAA CAA GTT TTG ATT       2049
Lys Gln Pro Leu His Lys Pro Leu Ala Val Glu Lys Gln Val Leu Ile
                425             430             435

CTC TAT GCA TTG ACT CAT GGT CAT CTT GAT AAT GTT CCA GTT GAT GAT       2097
Leu Tyr Ala Leu Thr His Gly His Leu Asp Asn Val Pro Val Asp Asp
            440             445             450

GTT CTT GAT TTT GAA ACT AAA ATG TTC GAT TTC TTC GAT GCA AAT TAT       2145
```

-continued

```
                Val Leu Asp Phe Glu Thr Lys Met Phe Asp Phe Phe Asp Ala Asn Tyr
                        455                 460                 465

GCA GAT CTC TTG AAC GTA ATT ACT GAC ACT AAA GAT TTG CCA GAA GAA                2193
Ala Asp Leu Leu Asn Val Ile Thr Asp Thr Lys Asp Leu Pro Glu Glu
        470                 475                 480

GCA AAA CTT GAC GAA GCA ATT AAA GCA TTC AAA AAT ACA ACG AAT TAT                2241
Ala Lys Leu Asp Glu Ala Ile Lys Ala Phe Lys Asn Thr Thr Asn Tyr
485                 490                 495                 500

TAATAAGGAG GCTAACTA ATG GGA GCT TCA CTT AAC GAA ATA AAA ACT AAG                2292
                    Met Gly Ala Ser Leu Asn Glu Ile Lys Thr Lys
                     1               5                  10

ATT GCG TCA ACA AAG AAA ACA AGT CAA ATC ACA GGT GCC ATG CAA ATG                2340
Ile Ala Ser Thr Lys Lys Thr Ser Gln Ile Thr Gly Ala Met Gln Met
            15                  20                  25

GTT TCT GCT GCT AAA CTT CAA AAA GCA GAA TCT CAC GCT AAA GCT TTT                2388
Val Ser Ala Ala Lys Leu Gln Lys Ala Glu Ser His Ala Lys Ala Phe
        30                  35                  40

CAG ACT TAT GCT GAA AAA GTA CGT AAG ATT ACG ACT GAC TTA GTT TCA                2436
Gln Thr Tyr Ala Glu Lys Val Arg Lys Ile Thr Thr Asp Leu Val Ser
    45                  50                  55

AGC GAT AAT GAG CCG GCC AAA AAT CCG ATG ATG ATT AAA CGT GAA GTC                2484
Ser Asp Asn Glu Pro Ala Lys Asn Pro Met Met Ile Lys Arg Glu Val
60                  65                  70                  75

AAG AAA ACT GGC TAT CTC GTT ATC ACA TCA GAT CGT GGG CTT GTT GGC                2532
Lys Lys Thr Gly Tyr Leu Val Ile Thr Ser Asp Arg Gly Leu Val Gly
            80                  85                  90

AGT TAT AAT TCA AAT ATT TTG AAG TCT GTT ATA AGT AAT ATA CGT AAA                2580
Ser Tyr Asn Ser Asn Ile Leu Lys Ser Val Ile Ser Asn Ile Arg Lys
        95                 100                 105

CGC CAC ACA AAT GAG AGT GAG TAT ACA ATA CTT GCC CTT GGT GGT ACG                2628
Arg His Thr Asn Glu Ser Glu Tyr Thr Ile Leu Ala Leu Gly Gly Thr
    110                 115                 120

GGA GCG GAC TTT TTC AAA GCC CGT AAC GTC AAA GTT TCT TAT GTT CTT                2676
Gly Ala Asp Phe Phe Lys Ala Arg Asn Val Lys Val Ser Tyr Val Leu
125                 130                 135

CGC GGA CTT TCA GAT CAA CCG ACC TTT GAA GAG GTT CGG GCA ATT GTT                2724
Arg Gly Leu Ser Asp Gln Pro Thr Phe Glu Glu Val Arg Ala Ile Val
140                 145                 150                 155

ACA GAA GCC GTA GAA GAA TAT CAA GCA GAA GAA TTC GAT GAA CTC TAT                2772
Thr Glu Ala Val Glu Glu Tyr Gln Ala Glu Glu Phe Asp Glu Leu Tyr
            160                 165                 170

GTT TGT TAC AAC CAC CAT GTG AAC TCA TTG GTA AGT GAG GCA CGG ATG                2820
Val Cys Tyr Asn His His Val Asn Ser Leu Val Ser Glu Ala Arg Met
        175                 180                 185

GAA AAA ATG TTA CCT ATT TCT TTT GAT GAA AAA GGT GAC GAA AAA GCA                2868
Glu Lys Met Leu Pro Ile Ser Phe Asp Glu Lys Gly Asp Glu Lys Ala
    190                 195                 200

TCT CTT GTT ACA TTT GAA TTA GAA CCA GAT CGT GAA ACA ATC TTA AAT                2916
Ser Leu Val Thr Phe Glu Leu Glu Pro Asp Arg Glu Thr Ile Leu Asn
205                 210                 215

CAG TTG TTG CCG CAA TAT GCT GAA AGT ATG ATT TAT GGC TCA ATT GTT                2964
Gln Leu Leu Pro Gln Tyr Ala Glu Ser Met Ile Tyr Gly Ser Ile Val
220                 225                 230                 235

GAT GCA AAA ACA GCA GAA CAT GCT GCA GGT ATG ACC GCA ATG CGT ACT                3012
Asp Ala Lys Thr Ala Glu His Ala Ala Gly Met Thr Ala Met Arg Thr
            240                 245                 250

GCA ACA GAT AAT GCA CAT TCT GTC ATT AAT GAT TTA ACC ATT CAA TAT                3060
Ala Thr Asp Asn Ala His Ser Val Ile Asn Asp Leu Thr Ile Gln Tyr
        255                 260                 265
```

```
                                          -continued

AAC CGT GCT CGT CAA GCT TCA ATT ACG CAA GAA ATT ACG GAA ATT GTT    3108
Asn Arg Ala Arg Gln Ala Ser Ile Thr Gln Glu Ile Thr Glu Ile Val
        270                 275                 280

GCG GGT GCT TCA GCG CTA TAATTACTGT CAAACATTAT TCTCAATGTT           3156
Ala Gly Ala Ser Ala Leu
        285

ACGATTTATC AACTTGAGGA ATAAATGTTC TGTCAGTAAA GGCTTTGAAT TTTAAATACG  3216

TTTGTCAGTA AATTTTTACT GATTAGCTTA AAAATGAATA GAAATTCTGT TGTTAGACAG  3276

AAAATAAAAA CAGGAGGAAA AACA TTG AGT TCT GGT AAA ATT ACT CAG GTT    3327
                            Leu Ser Ser Gly Lys Ile Thr Gln Val
                             1               5

ATC GGT CCC GTC GTT GAC GTG GAA TTT GGT TCT GAT GCC AAA CTG CCT    3375
Ile Gly Pro Val Val Asp Val Glu Phe Gly Ser Asp Ala Lys Leu Pro
 10              15                  20                  25

GAG ATT AAC AAT GCC TTG ATT GTC TAC AAA GAT GTC AAT GGT TTA AAA    3423
Glu Ile Asn Asn Ala Leu Ile Val Tyr Lys Asp Val Asn Gly Leu Lys
                 30                  35                  40

ACA AAA ATT ACT CTT GAA GTT GCT TTG GAA CTT GGT GAT GGT GCA GTT    3471
Thr Lys Ile Thr Leu Glu Val Ala Leu Glu Leu Gly Asp Gly Ala Val
             45                  50                  55

CGT ACG ATC GCT ATG GAA TCT ACT GAT GGA TTG ACT CGT GGA CTT GAA    3519
Arg Thr Ile Ala Met Glu Ser Thr Asp Gly Leu Thr Arg Gly Leu Glu
         60                  65                  70

GTC CTT GAT ACA GGT AAA GCG GTC AGC GTT CCT GTT GGT GAA TCT ACT    3567
Val Leu Asp Thr Gly Lys Ala Val Ser Val Pro Val Gly Glu Ser Thr
     75                  80                  85

CTT GGT CGT GTT TTT AAT GTC CTT GGT GAC GTT ATT GAT GGT GGA GAA    3615
Leu Gly Arg Val Phe Asn Val Leu Gly Asp Val Ile Asp Gly Gly Glu
 90                  95                 100                 105

GAT TTC CCT GCT GAT GCA GAA CGT AAT CCT ATC CAC AAG AAA GCT CCA    3663
Asp Phe Pro Ala Asp Ala Glu Arg Asn Pro Ile His Lys Lys Ala Pro
                110                 115                 120

ACT TTT GAC GAA TTG TCA ACT GCA AAT GAA GTT CTT GTA ACA GGG ATT    3711
Thr Phe Asp Glu Leu Ser Thr Ala Asn Glu Val Leu Val Thr Gly Ile
            125                 130                 135

AAA GTT GTC GAT TTA CTT GCC CCT TAT CTT AAA GGG GGA AAA GTC GGA    3759
Lys Val Val Asp Leu Leu Ala Pro Tyr Leu Lys Gly Gly Lys Val Gly
        140                 145                 150

CTC TTC GGT GGT GCC GGT GTT GGT AAA ACC GTC CTT ATC CAA GAA TTG    3807
Leu Phe Gly Gly Ala Gly Val Gly Lys Thr Val Leu Ile Gln Glu Leu
    155                 160                 165

ATT CAC AAT ATT GCC CAA GAA CAC GGT GGT ATT TCT GTA TTT ACA GGT    3855
Ile His Asn Ile Ala Gln Glu His Gly Gly Ile Ser Val Phe Thr Gly
170                 175                 180                 185

GTT GGC GAT CGT ACT CGT GAC GGG AAT GAC CTT TAC TGG GAA ATG AAA    3903
Val Gly Asp Arg Thr Arg Asp Gly Asn Asp Leu Tyr Trp Glu Met Lys
                190                 195                 200

GAA TCA GGC GTT ATT GAA AAA ACA GCC ATG GTC TTT GGT CAA ATG AAT    3951
Glu Ser Gly Val Ile Glu Lys Thr Ala Met Val Phe Gly Gln Met Asn
            205                 210                 215

GAA CCA CCT GGA GCA CGT ATG CGT GTT GCC CTT ACT GGT TTA ACA ATT    3999
Glu Pro Pro Gly Ala Arg Met Arg Val Ala Leu Thr Gly Leu Thr Ile
        220                 225                 230

GCG GAA TAT TTC CGT GAT GTT CAA GGA CAA GAC GTA TTG CTT TTC ATC    4047
Ala Glu Tyr Phe Arg Asp Val Gln Gly Gln Asp Val Leu Leu Phe Ile
    235                 240                 245

GAT AAC ATC TTC CGT TTC ACT CAA GCT GGT TCA GAA GTT TCT GCC CTT    4095
Asp Asn Ile Phe Arg Phe Thr Gln Ala Gly Ser Glu Val Ser Ala Leu
250                 255                 260                 265
```

```
TGG GGA CGT ATG CCT TCT GCC GTT GGT TAC CAA CCA ACT CTT GCA ACT      4143
Trp Gly Arg Met Pro Ser Ala Val Gly Tyr Gln Pro Thr Leu Ala Thr
                270                 275                 280

GAA ATG GTT CAA TTA CAG GAA CGT ATC ACT TCT ACT AAG AAG GGT TCT      4191
Glu Met Val Gln Leu Gln Glu Arg Ile Thr Ser Thr Lys Lys Gly Ser
            285                 290                 295

GTT ACA TCT ATC CCA GCG ATT TAT GTC CCT GCC GAT GAC TAT ACT GAC      4239
Val Thr Ser Ile Pro Ala Ile Tyr Val Pro Ala Asp Asp Tyr Thr Asp
        300                 305                 310

CCA GCG CCA GCT ACA GCC TTC GCT CAC TTG GAC GCA ACA ACT AAC TTG      4287
Pro Ala Pro Ala Thr Ala Phe Ala His Leu Asp Ala Thr Thr Asn Leu
    315                 320                 325

GAA CGT CGT TTG ACA CAA ATG GGT ATC TAT CCA GCC GTT GAC CCA CTT      4335
Glu Arg Arg Leu Thr Gln Met Gly Ile Tyr Pro Ala Val Asp Pro Leu
330                 335                 340                 345

GCT TCA TCA TCA CGT GCG CTT ACA CCT GAA ATT GTT GGT GAA GAA CAC      4383
Ala Ser Ser Ser Arg Ala Leu Thr Pro Glu Ile Val Gly Glu Glu His
                350                 355                 360

TAT GAA GTT GCA ATG GAA GTT CAA CGT GTC CTT CAA CGC TAC AAA GAA      4431
Tyr Glu Val Ala Met Glu Val Gln Arg Val Leu Gln Arg Tyr Lys Glu
            365                 370                 375

TTG CAA GAT ATC ATT GCC ATT CTT GGT ATG GAT GAA TTG TCA GAT GAT      4479
Leu Gln Asp Ile Ile Ala Ile Leu Gly Met Asp Glu Leu Ser Asp Asp
        380                 385                 390

GAA AAA ATT CTC GTT GGA CGT GCA CGT CGT ATC CAA TTC TTC CTT TCA      4527
Glu Lys Ile Leu Val Gly Arg Ala Arg Arg Ile Gln Phe Phe Leu Ser
    395                 400                 405

CAA AAC TTC CAC GTT GCT GAA CAG TTT ACT GGT CAA CCT GGT TCA TAT      4575
Gln Asn Phe His Val Ala Glu Gln Phe Thr Gly Gln Pro Gly Ser Tyr
410                 415                 420                 425

GTA CCA ATT GAC AAA ACA GTT CAT GAC TTC AAG GAA ATT TTG GAA GGT      4623
Val Pro Ile Asp Lys Thr Val His Asp Phe Lys Glu Ile Leu Glu Gly
                430                 435                 440

AAA TAT GAC GAA GTC CCT GAA GAT GCT TTC CGT GGA GTA GGT CCA ATT      4671
Lys Tyr Asp Glu Val Pro Glu Asp Ala Phe Arg Gly Val Gly Pro Ile
            445                 450                 455

GAA GAC GTA CTT GCA AAA GCA AAA TCA ATG GGT TAT TAATTCGATT           4717
Glu Asp Val Leu Ala Lys Ala Lys Ser Met Gly Tyr
        460                 465

TCTTATGAAA TGACAAAGTG AAAATACATT ATTGAATCGC AAAATTTACT GACAATAATT   4777

CTGTCGTAAG TGCTCACTTT TAAGTTGTTC CGATCGTT                            4815

(2) INFORMATION FOR SEQ ID NO: 2:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Lys Val Asn Ser Gln Lys Tyr Ser Lys Ala Leu Leu Glu Val
 1               5                  10                  15

Ala Arg Glu Lys Gly Gln Leu Glu Ala Ile Leu Thr Glu Val Ser Glu
            20                  25                  30

Met Ile Gln Leu Phe Lys Glu Asn Asn Leu Gly Ala Phe Leu Ala Asn
        35                  40                  45

Glu Val Tyr Ser Phe Ser Ala Lys Ser Glu Leu Ile Asp Thr Leu Leu
```

```
                50                  55                  60
Gln Thr Ser Ser Glu Val Met Ser Asn Phe Leu Asn Thr Ile Arg Ser
 65                  70                  75                  80

Asn Gly Arg Leu Ala Asp Leu Gly Ile Leu Glu Glu Thr Lys Asn
                 85                  90                  95

Ala Ala Asp Asp Met Phe Lys Ile Ala Asp Val Glu Val Val Ser Ser
                100                 105                 110

Ile Ala Leu Ser Glu Ala Gln Ile Glu Lys Phe Lys Ala Met Ala Lys
                115                 120                 125

Ser Lys Phe Asp Leu Asn Glu Val Thr Val Ile Asn Thr Val Asn Glu
130                 135                 140

Lys Ile Leu Gly Gly Phe Ile Val Asn Ser Arg Gly Lys Ile Ile Asp
145                 150                 155                 160

Ala Ser Leu Lys Thr Gln Leu Ala Lys Ile Ala Ala Glu Ile Leu
                165                 170                 175

(2) INFORMATION FOR SEQ ID NO: 3:

(i) SEQUENCE CHARACTERISTICS:
        (A) LENGTH: 500 amino acids
        (B) TYPE: amino acid
        (D) TOPOLOGY: linear (ii) MOLECULE TYPE: protein (xi) SEQUENCE DESCRIPTION: SEQ ID NO: 3:

Leu Ala Ile Lys Ala Asn Glu Ile Ser Ser Leu Ile Lys Lys Gln Ile
 1                   5                  10                  15

Glu Asn Phe Thr Pro Asp Phe Glu Val Ala Glu Thr Gly Val Val Thr
                 20                  25                  30

Tyr Val Gly Asp Gly Ile Ala Arg Ala Tyr Gly Leu Glu Asn Ala Met
                 35                  40                  45

Ser Gly Glu Leu Val Glu Phe Ser Asn Gly Ile Leu Gly Met Ala Gln
 50                  55                  60

Asn Leu Asp Ala Thr Asp Val Gly Ile Ile Val Leu Gly Asp Phe Leu
 65                  70                  75                  80

Ser Ile Arg Glu Gly Asp Thr Val Lys Arg Thr Gly Lys Ile Met Glu
                 85                  90                  95

Ile Gln Val Gly Glu Glu Leu Ile Gly Arg Val Val Asn Pro Leu Gly
                100                 105                 110

Gln Pro Val Asp Gly Leu Gly Glu Leu Asn Thr Gly Lys Thr Arg Pro
                115                 120                 125

Val Glu Ala Lys Ala Pro Gly Val Met Gln Arg Lys Ser Val Ser Glu
130                 135                 140

Pro Leu Gln Thr Gly Leu Lys Ala Ile Asp Ala Leu Val Pro Ile Gly
145                 150                 155                 160

Arg Gly Gln Arg Glu Leu Ile Ile Gly Asp Arg Gln Thr Gly Lys Thr
                165                 170                 175

Ser Val Ala Ile Asp Ala Ile Leu Asn Gln Lys Gly Gln Asp Met Ile
                180                 185                 190

Cys Ile Tyr Val Ala Ile Gly Gln Lys Glu Ser Thr Val Arg Thr Gln
                195                 200                 205

Val Glu Thr Leu Arg Lys Leu Gly Ala Met Asp Tyr Thr Ile Val Val
                210                 215                 220

Thr Ala Ser Ala Ser Gln Pro Ser Pro Leu Leu Tyr Ile Ala Pro Tyr
225                 230                 235                 240
```

```
Ala Gly Ala Ala Met Gly Glu Glu Phe Met Tyr Asn Gly Lys His Val
                245                 250                 255

Leu Val Val Tyr Asp Asp Leu Ser Lys Gln Ala Val Ala Tyr Arg Glu
            260                 265                 270

Leu Ser Leu Leu Leu Arg Arg Pro Pro Gly Arg Glu Ala Tyr Pro Gly
        275                 280                 285

Asp Val Phe Tyr Leu His Ser Arg Leu Leu Arg Ala Ala Lys Leu
    290                 295                 300

Ser Asp Asp Leu Gly Gly Ser Met Thr Ala Leu Pro Phe Ile Glu
305             310                 315                 320

Thr Gln Ala Gly Asp Ile Ser Ala Tyr Ile Pro Thr Asn Val Ile Ser
                325                 330                 335

Ile Thr Asp Gly Gln Ile Phe Leu Glu Asn Asp Leu Phe Tyr Ser Gly
            340                 345                 350

Val Arg Pro Ala Ile Asp Ala Gly Ser Ser Val Ser Arg Val Gly Gly
        355                 360                 365

Ala Ala Gln Ile Lys Ala Met Lys Lys Val Ala Gly Thr Leu Arg Leu
    370                 375                 380

Asp Leu Ala Ser Phe Arg Glu Leu Glu Ala Phe Thr Gln Phe Gly Ser
385             390                 395                 400

Asp Leu Asp Glu Ala Thr Gln Ala Lys Leu Asn Arg Gly Arg Arg Thr
                405                 410                 415

Val Glu Val Leu Lys Gln Pro Leu His Lys Pro Leu Ala Val Glu Lys
            420                 425                 430

Gln Val Leu Ile Leu Tyr Ala Leu Thr His Gly His Leu Asp Asn Val
        435                 440                 445

Pro Val Asp Asp Val Leu Asp Phe Glu Thr Lys Met Phe Asp Phe Phe
    450                 455                 460

Asp Ala Asn Tyr Ala Asp Leu Leu Asn Val Ile Thr Asp Thr Lys Asp
465             470                 475                 480

Leu Pro Glu Glu Ala Lys Leu Asp Glu Ala Ile Lys Ala Phe Lys Asn
                485                 490                 495

Thr Thr Asn Tyr
            500

(2) INFORMATION FOR SEQ ID NO: 4:

(i) SEQUENCE CHARACTERISTICS:
        (A) LENGTH: 289 amino acids
        (B) TYPE: amino acid
        (D) TOPOLOGY: linear (ii) MOLECULE TYPE: protein (xi) SEQUENCE DESCRIPTION: SEQ ID NO: 4:

Met Gly Ala Ser Leu Asn Glu Ile Lys Thr Lys Ile Ala Ser Thr Lys
 1               5                  10                  15

Lys Thr Ser Gln Ile Thr Gly Ala Met Gln Met Val Ser Ala Ala Lys
                20                  25                  30

Leu Gln Lys Ala Glu Ser His Ala Lys Ala Phe Gln Thr Tyr Ala Glu
            35                  40                  45

Lys Val Arg Lys Ile Thr Thr Asp Leu Val Ser Ser Asp Asn Glu Pro
        50                  55                  60

Ala Lys Asn Pro Met Met Ile Lys Arg Glu Val Lys Lys Thr Gly Tyr
65                  70                  75                  80
```

-continued

```
Leu Val Ile Thr Ser Asp Arg Gly Leu Val Gly Ser Tyr Asn Ser Asn
                85                  90                  95

Ile Leu Lys Ser Val Ile Ser Asn Ile Arg Lys Arg His Thr Asn Glu
            100                 105                 110

Ser Glu Tyr Thr Ile Leu Ala Leu Gly Gly Thr Gly Ala Asp Phe Phe
            115                 120                 125

Lys Ala Arg Asn Val Lys Val Ser Tyr Val Leu Arg Gly Leu Ser Asp
130                 135                 140

Gln Pro Thr Phe Glu Glu Val Arg Ala Ile Val Thr Glu Ala Val Glu
145                 150                 155                 160

Glu Tyr Gln Ala Glu Glu Phe Asp Glu Leu Tyr Val Cys Tyr Asn His
                165                 170                 175

His Val Asn Ser Leu Val Ser Glu Ala Arg Met Glu Lys Met Leu Pro
            180                 185                 190

Ile Ser Phe Asp Glu Lys Gly Asp Glu Lys Ala Ser Leu Val Thr Phe
            195                 200                 205

Glu Leu Glu Pro Asp Arg Glu Thr Ile Leu Asn Gln Leu Leu Pro Gln
    210                 215                 220

Tyr Ala Glu Ser Met Ile Tyr Gly Ser Ile Val Asp Ala Lys Thr Ala
225                 230                 235                 240

Glu His Ala Ala Gly Met Thr Ala Met Arg Thr Ala Thr Asp Asn Ala
                245                 250                 255

His Ser Val Ile Asn Asp Leu Thr Ile Gln Tyr Asn Arg Ala Arg Gln
            260                 265                 270

Ala Ser Ile Thr Gln Glu Ile Thr Glu Ile Val Ala Gly Ala Ser Ala
            275                 280                 285

Leu (2) INFORMATION FOR SEQ ID NO: 5:

(i) SEQUENCE CHARACTERISTICS:
        (A) LENGTH: 469 amino acids
        (B) TYPE: amino acid
        (D) TOPOLOGY: linear (ii) MOLECULE TYPE: protein (xi) SEQUENCE DESCRIPTION: SEQ ID NO: 5:

Leu Ser Ser Gly Lys Ile Thr Gln Val Ile Gly Pro Val Val Asp Val
1               5                   10                  15

Glu Phe Gly Ser Asp Ala Lys Leu Pro Glu Ile Asn Asn Ala Leu Ile
            20                  25                  30

Val Tyr Lys Asp Val Asn Gly Leu Lys Thr Lys Ile Thr Leu Glu Val
            35                  40                  45

Ala Leu Glu Leu Gly Asp Gly Ala Val Arg Thr Ile Ala Met Glu Ser
    50                  55                  60

Thr Asp Gly Leu Thr Arg Gly Leu Glu Val Leu Asp Thr Gly Lys Ala
65                  70                  75                  80

Val Ser Val Pro Val Gly Glu Ser Thr Leu Gly Arg Val Phe Asn Val
                85                  90                  95

Leu Gly Asp Val Ile Asp Gly Gly Glu Asp Phe Pro Ala Asp Ala Glu
            100                 105                 110

Arg Asn Pro Ile His Lys Lys Ala Pro Thr Phe Asp Glu Leu Ser Thr
            115                 120                 125

Ala Asn Glu Val Leu Val Thr Gly Ile Lys Val Val Asp Leu Leu Ala
130                 135                 140
```

```
Pro Tyr Leu Lys Gly Gly Lys Val Gly Leu Phe Gly Ala Gly Val
145                 150                 155                 160

Gly Lys Thr Val Leu Ile Gln Glu Leu Ile His Asn Ile Ala Gln Glu
            165                 170                 175

His Gly Gly Ile Ser Val Phe Thr Gly Val Gly Asp Arg Thr Arg Asp
                180                 185                 190

Gly Asn Asp Leu Tyr Trp Glu Met Lys Glu Ser Gly Val Ile Glu Lys
            195                 200                 205

Thr Ala Met Val Phe Gly Gln Met Asn Glu Pro Pro Gly Ala Arg Met
    210                 215                 220

Arg Val Ala Leu Thr Gly Leu Thr Ile Ala Glu Tyr Phe Arg Asp Val
225                 230                 235                 240

Gln Gly Gln Asp Val Leu Leu Phe Ile Asp Asn Ile Phe Arg Phe Thr
                245                 250                 255

Gln Ala Gly Ser Glu Val Ser Ala Leu Trp Gly Arg Met Pro Ser Ala
                260                 265                 270

Val Gly Tyr Gln Pro Thr Leu Ala Thr Glu Met Val Gln Leu Gln Glu
    275                 280                 285

Arg Ile Thr Ser Thr Lys Lys Gly Ser Val Thr Ser Ile Pro Ala Ile
    290                 295                 300

Tyr Val Pro Ala Asp Asp Tyr Thr Asp Pro Ala Pro Ala Thr Ala Phe
305                 310                 315                 320

Ala His Leu Asp Ala Thr Thr Asn Leu Glu Arg Arg Leu Thr Gln Met
                325                 330                 335

Gly Ile Tyr Pro Ala Val Asp Pro Leu Ala Ser Ser Arg Ala Leu
                340                 345                 350

Thr Pro Glu Ile Val Gly Glu Glu His Tyr Glu Val Ala Met Glu Val
            355                 360                 365

Gln Arg Val Leu Gln Arg Tyr Lys Glu Leu Gln Asp Ile Ile Ala Ile
    370                 375                 380

Leu Gly Met Asp Glu Leu Ser Asp Asp Glu Lys Ile Leu Val Gly Arg
385                 390                 395                 400

Ala Arg Arg Ile Gln Phe Phe Leu Ser Gln Asn Phe His Val Ala Glu
                405                 410                 415

Gln Phe Thr Gly Gln Pro Gly Ser Tyr Val Pro Ile Asp Lys Thr Val
            420                 425                 430

His Asp Phe Lys Glu Ile Leu Glu Gly Lys Tyr Asp Glu Val Pro Glu
            435                 440                 445

Asp Ala Phe Arg Gly Val Gly Pro Ile Glu Asp Val Leu Ala Lys Ala
    450                 455                 460

Lys Ser Met Gly Tyr
465

(2) INFORMATION FOR SEQ ID NO: 6:

(i) SEQUENCE CHARACTERISTICS:
        (A) LENGTH: 2207 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
    (A) ORGANISM: Lactococcus lactis subsp. lactis (ix) FEATURE:
    (A) NAME/KEY: CDS
    (B) LOCATION:4..633
    (D) OTHER INFORMATION:/partial
        /codon_start= 4
        /product= "ATPase subunit, partial sequence"
        /gene= "atpA"
        /standard_name= "alpha subunit of the F1 portion
        of the F0F1 ATPase"
        /label= alpha-subunit (ix) FEATURE:
    (A) NAME/KEY: CDS
    (B) LOCATION:652..1518
    (D) OTHER INFORMATION:/codon_start= 652
        /product= "ATPase subunit"
        /gene= "atpG"
        /standard_name= "gamma subunit of the F1 portion
        of the F0F1 ATPase"
        /label= gamma-subunit (ix) FEATURE:
    (A) NAME/KEY: CDS
    (B) LOCATION:1654..2205
    (D) OTHER INFORMATION:/partial
        /codon_start= 1654
        /product= "ATPase subunit, partial sequence"
        /gene= "atpD"
        /standard_name= "beta subunit of the F1 portion of
        the F0F1 ATPase"
        /label= beta-subunit (xi) SEQUENCE DESCRIPTION: SEQ ID NO: 6:

```
TGA TTC TAC TTA CAT TCA CGT CTT TTG GAA CGT GCT GCC AAA TTA TCT        48
    Phe Tyr Leu His Ser Arg Leu Leu Glu Arg Ala Ala Lys Leu Ser
    470                 475                 480

GAC TAT CTT GGT GGT GGT TCA ATG ACT GCA CTG CCA TTC ATT GAA ACA        96
Asp Tyr Leu Gly Gly Gly Ser Met Thr Ala Leu Pro Phe Ile Glu Thr
485                 490                 495                 500

CAA GCC GGA GAT ATC TCA GCT TAT ATT GCA ACA AAC GTT ATC TCT ATT       144
Gln Ala Gly Asp Ile Ser Ala Tyr Ile Ala Thr Asn Val Ile Ser Ile
                505                 510                 515

ACT GAC GGT CAA ATT TTC CTT GAA AAT GAC TTA TTC TAT TCA GGT GTA       192
Thr Asp Gly Gln Ile Phe Leu Glu Asn Asp Leu Phe Tyr Ser Gly Val
            520                 525                 530

CGT CCT GCC ATC GAT GCT GGT TCT TCA GTT TCT CGG GTT GGT GGT GCT       240
Arg Pro Ala Ile Asp Ala Gly Ser Ser Val Ser Arg Val Gly Gly Ala
        535                 540                 545

GCA CAG ATC AAA GCC ATG AAG AAA GTT GCT GGT ACT TTG CGT CTT GAC       288
Ala Gln Ile Lys Ala Met Lys Lys Val Ala Gly Thr Leu Arg Leu Asp
    550                 555                 560

CTT GCG TCA TTC CGT GAA CTT GAA GCC TTT ACT CAA TTT GGT TCT GAT       336
Leu Ala Ser Phe Arg Glu Leu Glu Ala Phe Thr Gln Phe Gly Ser Asp
565                 570                 575                 580

CTT GAT GAA GCG ACT CAA GCA AAA TTG AAT CGT GGT CGT CGT ACC GTT       384
Leu Asp Glu Ala Thr Gln Ala Lys Leu Asn Arg Gly Arg Arg Thr Val
                585                 590                 595

GAA GTT TTG AAG CAA CCA TTG CAC AAA CCA TTG GCT GTT GAA AAA CAA       432
Glu Val Leu Lys Gln Pro Leu His Lys Pro Leu Ala Val Glu Lys Gln
            600                 605                 610

GTT TTA ATT CTT TAT GCA TTG ACT CAT GGT CAC TTG GAT GAT GTT CCA       480
Val Leu Ile Leu Tyr Ala Leu Thr His Gly His Leu Asp Asp Val Pro
        615                 620                 625

GTT GAT GAC GTC CTT GAT TTT GAA ACA AAC AAT GTC CGA TTC TTC GAT       528
Val Asp Asp Val Leu Asp Phe Glu Thr Asn Asn Val Arg Phe Phe Asp
```

```
                    630                 635                 640
GCA AAT TAT GCA AAA CTC TTG AAC GTG ATT ACT GAA ACT AAA GAT TGC    576
Ala Asn Tyr Ala Lys Leu Leu Asn Val Ile Thr Glu Thr Lys Asp Cys
645                 650                 655                 660

CAG AAG AAG CAA AAC TCG ACG AAG CAA TTA AAG CAT TCT AAA ATA CAA    624
Gln Lys Lys Gln Asn Ser Thr Lys Gln Leu Lys His Ser Lys Ile Gln
                    665                 670                 675

CGA ATT ATT AATAAGGAGG CTAATCTA ATG GGA GCT TCA CTT AAT GAA ATA    675
Arg Ile Ile                             Met Gly Ala Ser Leu Asn Glu Ile
                                         1               5

AAA ACT AAG ATT GCC TCA ACG AAG AAA ACA AGT CAA ATA ACT GGA GCC    723
Lys Thr Lys Ile Ala Ser Thr Lys Lys Thr Ser Gln Ile Thr Gly Ala
        10                  15                  20

ATG CAA ATG GTT TCC GCT GCG AAA CTT CAA AAA GCT GAA TCT CAT GCC    771
Met Gln Met Val Ser Ala Ala Lys Leu Gln Lys Ala Glu Ser His Ala
25                  30                  35                  40

AAA GCA TTT CAA ATT TAT GCT GAA AAA GTT CGT AAA ATT ACA ACT GAT    819
Lys Ala Phe Gln Ile Tyr Ala Glu Lys Val Arg Lys Ile Thr Thr Asp
                    45                  50                  55

TTA GTT TCC TCT GAC AAA GAG CCA GCT AAG AAT CCA ATG ATG ATA GGA    867
Leu Val Ser Ser Asp Lys Glu Pro Ala Lys Asn Pro Met Met Ile Gly
            60                  65                  70

AGA GAA GTC AAA AAA ACT GGC TAT CTT GTA ATT ACT TCG GAT CGT GGA    915
Arg Glu Val Lys Lys Thr Gly Tyr Leu Val Ile Thr Ser Asp Arg Gly
        75                  80                  85

CTT GTC GGT GGC TAT AAT TCA TAT ATT TTG AAA TCT GTC ATG AAT ACT    963
Leu Val Gly Gly Tyr Asn Ser Tyr Ile Leu Lys Ser Val Met Asn Thr
90                  95                  100

ATC CGT AAA CGT CCT GCT AAT GAA AGT GAA TAT ACT ATT CTT GCA CTT    1011
Ile Arg Lys Arg Pro Ala Asn Glu Ser Glu Tyr Thr Ile Leu Ala Leu
105                 110                 115                 120

GGC GGT ACT GGA GCA GAT TTC TTC GGA GCA AGC AAT GTT AAA AGT TTC    1059
Gly Gly Thr Gly Ala Asp Phe Phe Gly Ala Ser Asn Val Lys Ser Phe
            125                 130                 135

TTA GTC CTT TGT GGT TTT TCA GAC CAA CCA AAT TTT GAA GAA GTT AGA    1107
Leu Val Leu Cys Gly Phe Ser Asp Gln Pro Asn Phe Glu Glu Val Arg
        140                 145                 150

GCG ATT GTT ACA GAA GCG GTA ACT GAA TAT CAA GCA GAA GAA TTT GAT    1155
Ala Ile Val Thr Glu Ala Val Thr Glu Tyr Gln Ala Glu Glu Phe Asp
    155                 160                 165

GAA CTT TAT GTT TGC TAT AAT CAC CAT GTG AAC TCA TTG GTA AGT GAA    1203
Glu Leu Tyr Val Cys Tyr Asn His His Val Asn Ser Leu Val Ser Glu
170                 175                 180

GCA AGT ATG GAA AAA ATG TTG CCT ATT TTT TTT GAA GCA TCA GGT CAA    1251
Ala Ser Met Glu Lys Met Leu Pro Ile Phe Phe Glu Ala Ser Gly Gln
185                 190                 195                 200

CAA AAA CCA TTT TTT GAA ACA TTT GAA TTA GAA CCA GAT TGT GAA ACA    1299
Gln Lys Pro Phe Phe Glu Thr Phe Glu Leu Glu Pro Asp Cys Glu Thr
            205                 210                 215

ATT TTA AAC CAA TTG TTG CCA CCA TAC GCT GAA AGT ATG ATT TAT GGT    1347
Ile Leu Asn Gln Leu Leu Pro Pro Tyr Ala Glu Ser Met Ile Tyr Gly
        220                 225                 230

TCA ATC GTT GAT GCT AAG ACA GCA GAA CAT GCT GCA GGT ATG ACA GCA    1395
Ser Ile Val Asp Ala Lys Thr Ala Glu His Ala Ala Gly Met Thr Ala
    235                 240                 245

ATG CGT ACT GCA ACT GAT AAT GCT CAC TCT GTT ATC AAT GAT TTG ACT    1443
Met Arg Thr Ala Thr Asp Asn Ala His Ser Val Ile Asn Asp Leu Thr
250                 255                 260

ATT CAA TAC AAC CGT GCT CGT CAA GCA TCG ATT ACG CAA GAA ATT ACG    1491
```

```
                                     -continued

Ile Gln Tyr Asn Arg Ala Arg Gln Ala Ser Ile Thr Gln Glu Ile Thr
265                 270                 275                 280

GAA ATC GTT GCA GGA GCC TCA GCG CTT TAATTTACTG ATAGGAATTC            1538
Glu Ile Val Ala Gly Ala Ser Ala Leu
                285

TGTCAGTGAT GGCTTTGAAT CTTAATTGTT TTTGTCAGTA AAATTTTTAC TGACAAACAT   1598

AAAAATGAAT AGAAATTCTG TTCTTTGACA GAAATAAAA ACAGGAGGAA AAACA TTG    1656
                                                              Leu
                                                                1

AGT TCT GGT AAA ATT ACT CAG ATT ATC GGT CCC GTC GTT GAC GTG GAA     1704
Ser Ser Gly Lys Ile Thr Gln Ile Ile Gly Pro Val Val Asp Val Glu
            5                  10                  15

TTT GGT TCT GAT GCC AAA TTG CCT GAG ATT AAC AAT GCC TTG ATT GTC     1752
Phe Gly Ser Asp Ala Lys Leu Pro Glu Ile Asn Asn Ala Leu Ile Val
            20                  25                  30

TAC AAA GAT GTC AAT GGC CTA AAA ACA AAA ATT ACT CTT GAA GTT GCT     1800
Tyr Lys Asp Val Asn Gly Leu Lys Thr Lys Ile Thr Leu Glu Val Ala
        35                  40                  45

TTG GAA CTT GGT GAT GGT GCA GTT CGT ACA ATC GCT ATG GAA TCT ACT     1848
Leu Glu Leu Gly Asp Gly Ala Val Arg Thr Ile Ala Met Glu Ser Thr
50                  55                  60                  65

GAT GGC TTG ACT CGT GGA CTT GAA GTC CTT GAT ACA GGT AAA GCA GTC     1896
Asp Gly Leu Thr Arg Gly Leu Glu Val Leu Asp Thr Gly Lys Ala Val
                70                  75                  80

AGC GTT CCT GTT GGG GAA GCC ACT CTT GGT CGT GTT TTT AAC GTC CTT     1944
Ser Val Pro Val Gly Glu Ala Thr Leu Gly Arg Val Phe Asn Val Leu
            85                  90                  95

GGT GAT GTT ATT GAC GGT GGG GAA GAA TTT GCT GCT GAT GCA GAA CGT     1992
Gly Asp Val Ile Asp Gly Gly Glu Glu Phe Ala Ala Asp Ala Glu Arg
            100                 105                 110

AAT CCT ATC CAT AAA AAA GCT CCA ACA TTT GAC GAA TTG TCA ACT GCA     2040
Asn Pro Ile His Lys Lys Ala Pro Thr Phe Asp Glu Leu Ser Thr Ala
115                 120                 125

AAC GAA GTT CTC GTA ACT GGG ATT AAA GTT GTC GAT TTG CTT GCA CCT     2088
Asn Glu Val Leu Val Thr Gly Ile Lys Val Val Asp Leu Leu Ala Pro
130                 135                 140                 145

TAC CTT AAA GGT GGT AAA GTT GGA CTT TTC GGT GGT GCC GGA GTT GGT     2136
Tyr Leu Lys Gly Gly Lys Val Gly Leu Phe Gly Gly Ala Gly Val Gly
                150                 155                 160

AAA GCC GTC CTT ATT CAA GAA TTG AAA CAC AAC ATC GCC CAA GAA CAC     2184
Lys Ala Val Leu Ile Gln Glu Leu Lys His Asn Ile Ala Gln Glu His
            165                 170                 175

GGA GGT ATT TCT GTG TTT ACC GG                                      2207
Gly Gly Ile Ser Val Phe Thr
        180

(2) INFORMATION FOR SEQ ID NO: 7:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 7:

Phe Tyr Leu His Ser Arg Leu Leu Glu Arg Ala Ala Lys Leu Ser Asp
 1               5                  10                  15

Tyr Leu Gly Gly Gly Ser Met Thr Ala Leu Pro Phe Ile Glu Thr Gln
            20                  25                  30
```

-continued

```
Ala Gly Asp Ile Ser Ala Tyr Ile Ala Thr Asn Val Ile Ser Ile Thr
            35                  40                  45

Asp Gly Gln Ile Phe Leu Glu Asn Asp Leu Phe Tyr Ser Gly Val Arg
         50                  55                  60

Pro Ala Ile Asp Ala Gly Ser Ser Val Ser Arg Val Gly Gly Ala Ala
 65                  70                  75                  80

Gln Ile Lys Ala Met Lys Lys Val Ala Gly Thr Leu Arg Leu Asp Leu
                 85                  90                  95

Ala Ser Phe Arg Glu Leu Glu Ala Phe Thr Gln Phe Gly Ser Asp Leu
            100                 105                 110

Asp Glu Ala Thr Gln Ala Lys Leu Asn Arg Gly Arg Thr Val Glu
        115                 120                 125

Val Leu Lys Gln Pro Leu His Lys Pro Leu Ala Val Glu Lys Gln Val
130                 135                 140

Leu Ile Leu Tyr Ala Leu Thr His Gly His Leu Asp Asp Val Pro Val
145                 150                 155                 160

Asp Asp Val Leu Asp Phe Glu Thr Asn Asn Val Arg Phe Phe Asp Ala
                165                 170                 175

Asn Tyr Ala Lys Leu Leu Asn Val Ile Thr Glu Thr Lys Asp Cys Gln
            180                 185                 190

Lys Lys Gln Asn Ser Thr Lys Gln Leu Lys His Ser Lys Ile Gln Arg
        195                 200                 205

Ile Ile
    210
```

(2) INFORMATION FOR SEQ ID NO: 8:

(i) SEQUENCE CHARACTERISTICS:
       (A) LENGTH: 289 amino acids
       (B) TYPE: amino acid
       (D) TOPOLOGY: linear (ii) MOLECULE TYPE: protein (xi) SEQUENCE DESCRIPTION: SEQ ID NO: 8:

```
Met Gly Ala Ser Leu Asn Glu Ile Lys Thr Lys Ile Ala Ser Thr Lys
 1               5                  10                  15

Lys Thr Ser Gln Ile Thr Gly Ala Met Gln Met Val Ser Ala Ala Lys
             20                  25                  30

Leu Gln Lys Ala Glu Ser His Ala Lys Ala Phe Gln Ile Tyr Ala Glu
            35                  40                  45

Lys Val Arg Lys Ile Thr Thr Asp Leu Val Ser Ser Asp Lys Glu Pro
         50                  55                  60

Ala Lys Asn Pro Met Met Ile Gly Arg Glu Val Lys Lys Thr Gly Tyr
 65                  70                  75                  80

Leu Val Ile Thr Ser Asp Arg Gly Leu Val Gly Gly Tyr Asn Ser Tyr
                 85                  90                  95

Ile Leu Lys Ser Val Met Asn Thr Ile Arg Lys Arg Pro Ala Asn Glu
            100                 105                 110

Ser Glu Tyr Thr Ile Leu Ala Leu Gly Gly Thr Gly Ala Asp Phe Phe
        115                 120                 125

Gly Ala Ser Asn Val Lys Ser Phe Leu Val Leu Cys Gly Phe Ser Asp
130                 135                 140

Gln Pro Asn Phe Glu Glu Val Arg Ala Ile Val Thr Glu Ala Val Thr
145                 150                 155                 160

Glu Tyr Gln Ala Glu Glu Phe Asp Glu Leu Tyr Val Cys Tyr Asn His
```

```
                      165                 170                 175
His Val Asn Ser Leu Val Ser Glu Ala Ser Met Glu Lys Met Leu Pro
            180                 185                 190

Ile Phe Phe Glu Ala Ser Gly Gln Gln Lys Pro Phe Phe Glu Thr Phe
            195                 200                 205

Glu Leu Glu Pro Asp Cys Glu Thr Ile Leu Asn Gln Leu Leu Pro Pro
            210                 215                 220

Tyr Ala Glu Ser Met Ile Tyr Gly Ser Ile Val Asp Ala Lys Thr Ala
225                 230                 235                 240

Glu His Ala Ala Gly Met Thr Ala Met Arg Thr Ala Thr Asp Asn Ala
            245                 250                 255

His Ser Val Ile Asn Asp Leu Thr Ile Gln Tyr Asn Arg Ala Arg Gln
            260                 265                 270

Ala Ser Ile Thr Gln Glu Ile Thr Glu Ile Val Ala Gly Ala Ser Ala
            275                 280                 285

Leu
```

(2) INFORMATION FOR SEQ ID NO: 9:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO: 9:

```
Leu Ser Ser Gly Lys Ile Thr Gln Ile Ile Gly Pro Val Val Asp Val
1               5                   10                  15

Glu Phe Gly Ser Asp Ala Lys Leu Pro Glu Ile Asn Asn Ala Leu Ile
            20                  25                  30

Val Tyr Lys Asp Val Asn Gly Leu Lys Thr Lys Ile Thr Leu Glu Val
        35                  40                  45

Ala Leu Glu Leu Gly Asp Gly Ala Val Arg Thr Ile Ala Met Glu Ser
    50                  55                  60

Thr Asp Gly Leu Thr Arg Gly Leu Glu Val Leu Asp Thr Gly Lys Ala
65                  70                  75                  80

Val Ser Val Pro Val Gly Glu Ala Thr Leu Gly Arg Val Phe Asn Val
            85                  90                  95

Leu Gly Asp Val Ile Asp Gly Gly Glu Glu Phe Ala Ala Asp Ala Glu
            100                 105                 110

Arg Asn Pro Ile His Lys Lys Ala Pro Thr Phe Asp Glu Leu Ser Thr
            115                 120                 125

Ala Asn Glu Val Leu Val Thr Gly Ile Lys Val Val Asp Leu Leu Ala
        130                 135                 140

Pro Tyr Leu Lys Gly Gly Lys Val Gly Leu Phe Gly Gly Ala Gly Val
145                 150                 155                 160

Gly Lys Ala Val Leu Ile Gln Glu Leu Lys His Asn Ile Ala Gln Glu
            165                 170                 175

His Gly Gly Ile Ser Val Phe Thr
            180
```

(2) INFORMATION FOR SEQ ID NO: 10:

(i) SEQUENCE CHARACTERISTICS:
        (A) LENGTH: 2161 base pairs
        (B) TYPE: nucleic acid (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus thermophilus
        (B) STRAIN: ST3

(ix) FEATURE:
        (A) NAME/KEY: CDS
        (B) LOCATION:2..637
        (D) OTHER INFORMATION:/partial
            /codon_start= 2
            /product= "ATPase subunit, partial sequence"
            /gene= "atpA"
            /standard_name= "alpha subunit of the F1 portion
            of the F0F1 ATPase"
            /label= alpha-subunit (ix) FEATURE:
        (A) NAME/KEY: CDS
        (B) LOCATION:659..1537
        (D) OTHER INFORMATION:/codon_start= 659
            /product= "ATPase subunit"
            /gene= "atpG"
            /standard_name= "gamma subunit of the F1 portion
            of the F0F1 ATPase"
            /label= gamma-subunit (ix) FEATURE:
        (A) NAME/KEY: CDS
        (B) LOCATION:1616..2161
        (D) OTHER INFORMATION:/partial
            /codon_start= 1616
            /product= "ATPase subunit, partial sequence"
            /gene= "atpD"
            /standard_name= "beta subunit of the F1 portion of
            the F0F1 ATPase"
            /label= beta-subunit (xi) SEQUENCE DESCRIPTION: SEQ ID NO: 10:

```
T GAT TCT CAT CTC CAC TCA CGT CTT TTG GAA CGT TCA GCT AAG CTT           46
  Asp Ser His Leu His Ser Arg Leu Leu Glu Arg Ser Ala Lys Leu
  185             190                 195

TCA GAT GAT CTT GGT GGT GGT TCA ATG ACT GCC TTG CCA ATC ATC CAA         94
Ser Asp Asp Leu Gly Gly Gly Ser Met Thr Ala Leu Pro Ile Ile Gln
200             205                 210                 215

ACA CAA GCA GGA GAT ATC TCA GCT TAT ATC GCG ACA AAC GTT ATT TCT        142
Thr Gln Ala Gly Asp Ile Ser Ala Tyr Ile Ala Thr Asn Val Ile Ser
                220                 225                 230

ATC ACA GAT GGA CAA ATC TTC TTG CAA GAA AAT CTT TTC AAC TCA GGT        190
Ile Thr Asp Gly Gln Ile Phe Leu Gln Glu Asn Leu Phe Asn Ser Gly
            235                 240                 245

ATT CGT CCT GCG ATT GAT GCT GGT TCT TCA GTA TCA CGT GTT GGT GGT        238
Ile Arg Pro Ala Ile Asp Ala Gly Ser Ser Val Ser Arg Val Gly Gly
        250                 255                 260

TCA GCA CAA ATC AAA GCA ATG AAG AAA GTT GCT GGT ACC CTT CGT CTT        286
Ser Ala Gln Ile Lys Ala Met Lys Lys Val Ala Gly Thr Leu Arg Leu
    265                 270                 275

GAC TTG GCT TCT CAC CGT GAA CTT GAA GCC TTT ACA CAA TTC GGT TCT        334
Asp Leu Ala Ser His Arg Glu Leu Glu Ala Phe Thr Gln Phe Gly Ser
280                 285                 290                 295

GAT TTG GAT GCC GCA ACA CAA GCT AAA CTT AAT CGT GGA CGT CGT ACA        382
Asp Leu Asp Ala Ala Thr Gln Ala Lys Leu Asn Arg Gly Arg Arg Thr
                300                 305                 310
```

|     |     |     |     |     |     |     |     |     |     |     |     |     |     |     |     | |
|-----|-----|-----|-----|-----|-----|-----|-----|-----|-----|-----|-----|-----|-----|-----|-----|---|
| GTT | GAA | GTG | CTT | AAA | CAA | CCA | CTT | CAT | AAC | CCA | CTT | CCG | GTT | GAA | AAA | 430 |
| Val | Glu | Val | Leu | Lys | Gln | Pro | Leu | His | Asn | Pro | Leu | Pro | Val | Glu | Lys | |
|     |     |     |     | 315 |     |     |     | 320 |     |     |     | 325 |     |     |     | |
| CAA | GTT | CTT | ATT | CTT | TAC | GCT | TTG | ACA | CAT | GGC | TTC | TTG | GAC | AGT | GTT | 478 |
| Gln | Val | Leu | Ile | Leu | Tyr | Ala | Leu | Thr | His | Gly | Phe | Leu | Asp | Ser | Val | |
|     | 330 |     |     |     |     | 335 |     |     |     |     | 340 |     |     |     |     | |
| CCG | GTT | GAT | CAA | ATC | TTG | GAT | TTT | GAA | GAA | GCC | CTC | TAT | GAC | TAC | TTT | 526 |
| Pro | Val | Asp | Gln | Ile | Leu | Asp | Phe | Glu | Glu | Ala | Leu | Tyr | Asp | Tyr | Phe | |
| 345 |     |     |     |     | 350 |     |     |     |     | 355 |     |     |     |     |     | |
| GAT | AGC | CAT | CAT | GAG | GAT | ATC | TTT | GAA | ACA | ATC | CGT | TCA | ACT | AAG | GAT | 574 |
| Asp | Ser | His | His | Glu | Asp | Ile | Phe | Glu | Thr | Ile | Arg | Ser | Thr | Lys | Asp | |
| 360 |     |     |     |     | 365 |     |     |     |     | 370 |     |     |     |     | 375 | |
| CTT | CCT | GAA | GAA | GCT | GTG | CTT | AAT | GAA | GCT | ATC | CAA | GCT | TTC | AAA | GAT | 622 |
| Leu | Pro | Glu | Glu | Ala | Val | Leu | Asn | Glu | Ala | Ile | Gln | Ala | Phe | Lys | Asp | |
|     |     |     |     | 380 |     |     |     |     | 385 |     |     |     |     | 390 |     | |
| CAA | TCG | GAA | TAC | AAA | TAGAGATAGG | GAGGACAGCA | T | ATG | GCA | GGC | TCT | CTA | | | | 673 |
| Gln | Ser | Glu | Tyr | Lys |     |     |     | Met | Ala | Gly | Ser | Leu | | | | |
|     |     |     |     | 395 |     |     |     | 1   |     |     |     | 5   | | | | |
| AGA | GAA | ATC | AAA | GCA | AAA | ATT | GCT | TCA | ATT | AAG | CAA | ACG | AGT | CAT | ATT | 721 |
| Arg | Glu | Ile | Lys | Ala | Lys | Ile | Ala | Ser | Ile | Lys | Gln | Thr | Ser | His | Ile | |
|     |     |     | 10  |     |     |     |     | 15  |     |     |     |     | 20  |     |     | |
| ACA | GGA | GCC | ATG | CAA | ATG | GTT | TCT | GCT | TCT | AAA | TTG | ACA | CGT | TCT | GAG | 769 |
| Thr | Gly | Ala | Met | Gln | Met | Val | Ser | Ala | Ser | Lys | Leu | Thr | Arg | Ser | Glu | |
|     |     |     |     | 25  |     |     |     |     | 30  |     |     |     |     | 35  |     | |
| CAG | GCT | GCT | AAA | GAT | TTC | CAA | ATC | TAT | GCC | TCA | AAA | ATT | AGA | CAG | ATC | 817 |
| Gln | Ala | Ala | Lys | Asp | Phe | Gln | Ile | Tyr | Ala | Ser | Lys | Ile | Arg | Gln | Ile | |
|     |     | 40  |     |     |     |     | 45  |     |     |     |     | 50  |     |     |     | |
| ACA | ACA | GAT | CTT | CTA | CAT | TCA | GAA | TTG | GTT | AAT | GGT | TCT | TCA | AAT | CCG | 865 |
| Thr | Thr | Asp | Leu | Leu | His | Ser | Glu | Leu | Val | Asn | Gly | Ser | Ser | Asn | Pro | |
|     | 55  |     |     |     |     | 60  |     |     |     |     | 65  |     |     |     |     | |
| ATG | TTG | GAT | GCA | CGT | CCA | GTT | CGT | AAG | TCA | GGG | TAT | ATT | GTC | ATT | ACT | 913 |
| Met | Leu | Asp | Ala | Arg | Pro | Val | Arg | Lys | Ser | Gly | Tyr | Ile | Val | Ile | Thr | |
| 70  |     |     |     |     | 75  |     |     |     |     | 80  |     |     |     |     | 85  | |
| TCA | GAT | AAG | GGA | TTA | GTT | GGA | GGA | TAT | AAT | TCA | ACC | ATT | CTT | AAA | GCT | 961 |
| Ser | Asp | Lys | Gly | Leu | Val | Gly | Gly | Tyr | Asn | Ser | Thr | Ile | Leu | Lys | Ala | |
|     |     |     |     | 90  |     |     |     |     | 95  |     |     |     |     | 100 |     | |
| GTC | TTG | GAT | ATG | ATT | AAA | CGT | GAC | CAT | GAT | TCT | GAA | GAT | GAA | TAT | GCT | 1009 |
| Val | Leu | Asp | Met | Ile | Lys | Arg | Asp | His | Asp | Ser | Glu | Asp | Glu | Tyr | Ala | |
|     |     |     |     | 105 |     |     |     |     | 110 |     |     |     |     | 115 |     | |
| ATC | ATC | TCT | ATT | GGT | GGA | ACA | GGT | TCA | GAT | TTC | TTC | AAA | GCT | CGT | AAC | 1057 |
| Ile | Ile | Ser | Ile | Gly | Gly | Thr | Gly | Ser | Asp | Phe | Phe | Lys | Ala | Arg | Asn | |
|     |     | 120 |     |     |     |     | 125 |     |     |     |     | 130 |     |     |     | |
| ATG | AAT | GTT | GCT | TTT | GAA | CTT | CGT | GGC | CTT | GAA | GAT | CAA | CCT | AGT | TTC | 1105 |
| Met | Asn | Val | Ala | Phe | Glu | Leu | Arg | Gly | Leu | Glu | Asp | Gln | Pro | Ser | Phe | |
| 135 |     |     |     |     | 140 |     |     |     |     | 145 |     |     |     |     |     | |
| GAT | CAA | GTC | GGG | GAA | ATC | ATT | CTA | AAA | GCT | GTA | GGA | ATG | TAT | CAA | AAT | 1153 |
| Asp | Gln | Val | Gly | Glu | Ile | Ile | Leu | Lys | Ala | Val | Gly | Met | Tyr | Gln | Asn | |
| 150 |     |     |     |     | 155 |     |     |     |     | 160 |     |     |     |     | 165 | |
| GAG | CTT | TTT | GAT | GAA | CTT | TAT | GTG | TGT | TAC | AAT | CAT | CAT | ATT | AAT | AGT | 1201 |
| Glu | Leu | Phe | Asp | Glu | Leu | Tyr | Val | Cys | Tyr | Asn | His | His | Ile | Asn | Ser | |
|     |     |     |     | 170 |     |     |     |     | 175 |     |     |     |     | 180 |     | |
| TTG | TTT | TGT | GAA | GTT | TGT | GTT | GAA | AAA | ATG | CTT | CCA | ATT | GCT | GAT | TTT | 1249 |
| Leu | Phe | Cys | Glu | Val | Cys | Val | Glu | Lys | Met | Leu | Pro | Ile | Ala | Asp | Phe | |
|     |     |     |     | 185 |     |     |     |     | 190 |     |     |     |     | 195 |     | |
| GAT | CCT | AAT | GAA | TTT | GAA | GGC | CAT | GTA | TTG | ACC | AAG | TTT | GAA | TTG | GAA | 1297 |
| Asp | Pro | Asn | Glu | Phe | Glu | Gly | His | Val | Leu | Thr | Lys | Phe | Glu | Leu | Glu | |
|     |     |     | 200 |     |     |     |     | 205 |     |     |     |     | 210 |     |     | |
| CCA | AGT | TGT | GAT | ACT | ATT | TTG | GAT | CAA | CTT | TTG | CCC | ACA | ATA | GTC | GGT | 1345 |
| Pro | Ser | Cys | Asp | Thr | Ile | Leu | Asp | Gln | Leu | Leu | Pro | Thr | Ile | Val | Gly | |
|     |     | 215 |     |     |     |     | 220 |     |     |     |     | 225 |     |     |     | |

-continued

```
GAG AGT TTT ATC TAC GGT GCT ATC GTA GAT GCC AAA ACA GCT GAG CAT       1393
Glu Ser Phe Ile Tyr Gly Ala Ile Val Asp Ala Lys Thr Ala Glu His
230                 235                 240                 245

GCT GCT GGT ATG ACC GCA ATG CAG ACT GCC ACT GAT AAT GCT AAG AAA       1441
Ala Ala Gly Met Thr Ala Met Gln Thr Ala Thr Asp Asn Ala Lys Lys
                250                 255                 260

ATA ATT AAC GAT TTA ACA ATT CAA TAC AAC CGT GCA CGT CAA GCA GCC       1489
Ile Ile Asn Asp Leu Thr Ile Gln Tyr Asn Arg Ala Arg Gln Ala Ala
            265                 270                 275

ATT ACT CAG GAA ATC ACT GAG ATT GTT GGC GGT GCT AGT GCA CTT GAA       1537
Ile Thr Gln Glu Ile Thr Glu Ile Val Gly Gly Ala Ser Ala Leu Glu
        280                 285                 290

TAGCTAGAGA TTTGTCTTGA TTTGACATAC AATAAAAAGG GATGATTGTC ATCCAGAAAA     1597

CTTCATAAGG AGAAAACA ATG AGC TCA GGC AAA ATT GCT CAG GTT GTT GGT      1648
                    Met Ser Ser Gly Lys Ile Ala Gln Val Val Gly
                     1               5                  10

CCT GTT GTA GAC GTA GCG TTT GCA ACT GGC GAT AAA CTT CCT GAG ATT       1696
Pro Val Val Asp Val Ala Phe Ala Thr Gly Asp Lys Leu Pro Glu Ile
                 15                  20                  25

AAC AAT GCA TTG GTC GTT TAC ACT GAG AAG AAA AGT CTT AGA CGG ATG       1744
Asn Asn Ala Leu Val Val Tyr Thr Glu Lys Lys Ser Leu Arg Arg Met
             30                  35                  40

GTG CTC GAA GTA GCT TCG TTG AAA CTT GGA GAA GGT GTG GTT CGT ACC       1792
Val Leu Glu Val Ala Ser Leu Lys Leu Gly Glu Gly Val Val Arg Thr
         45                  50                  55

ATT GCC ATG GAA TCT ACT GAT GGA TTG ACT CGT GGG CTA GAA GTT CTG       1840
Ile Ala Met Glu Ser Thr Asp Gly Leu Thr Arg Gly Leu Glu Val Leu
 60                  65                  70                  75

GAC ACA GGT CGT CCA ATC AGT GTT CCT GTT GGT AAA GAA CTT CTT GGA       1888
Asp Thr Gly Arg Pro Ile Ser Val Pro Val Gly Lys Glu Leu Leu Gly
                 80                  85                  90

CGT GTC TTT AAC GTG CTT GGA GAT ACC ATT GAC ATG GAA GCA CCT TTT       1936
Arg Val Phe Asn Val Leu Gly Asp Thr Ile Asp Met Glu Ala Pro Phe
             95                 100                 105

GCA GAT GAT GCA GAG CGT GAA CCA ATT CAT AAA AAA GCA CCT ACC TTC       1984
Ala Asp Asp Ala Glu Arg Glu Pro Ile His Lys Lys Ala Pro Thr Phe
         110                 115                 120

GAT GAA TTG TCA ACA AGT ACT GAA ATC CTT GAA ACA GGG ATT AAA GTT       2032
Asp Glu Leu Ser Thr Ser Thr Glu Ile Leu Glu Thr Gly Ile Lys Val
 125                 130                 135

ATC GAC TTG CTT GCC CCT TAT CTT AAA GGT GGT AAA GTC GGA CTT TTC       2080
Ile Asp Leu Leu Ala Pro Tyr Leu Lys Gly Gly Lys Val Gly Leu Phe
 140                 145                 150                 155

GGT GGT GCC GGT GTT GGT AAG GCC GTT CTT ATT CAA GAG CTG AAT CAC       2128
Gly Gly Ala Gly Val Gly Lys Ala Val Leu Ile Gln Glu Leu Asn His
                 160                 165                 170

AAC ATT GCT CAA GAA CAC GGT GGC ATT TCC GTG                            2161
Asn Ile Ala Gln Glu His Gly Gly Ile Ser Val
         175                 180
```

(2) INFORMATION FOR SEQ ID NO: 11:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO: 11:

```
Asp Ser His Leu His Ser Arg Leu Leu Glu Arg Ser Ala Lys Leu Ser
 1               5                  10                  15

Asp Asp Leu Gly Gly Ser Met Thr Ala Leu Pro Ile Ile Gln Thr
            20                  25                  30

Gln Ala Gly Asp Ile Ser Ala Tyr Ile Ala Thr Asn Val Ile Ser Ile
        35                  40                  45

Thr Asp Gly Gln Ile Phe Leu Gln Glu Asn Leu Phe Asn Ser Gly Ile
    50                  55                  60

Arg Pro Ala Ile Asp Ala Gly Ser Ser Val Ser Arg Val Gly Gly Ser
 65              70                  75                  80

Ala Gln Ile Lys Ala Met Lys Lys Val Ala Gly Thr Leu Arg Leu Asp
                85                  90                  95

Leu Ala Ser His Arg Glu Leu Glu Ala Phe Thr Gln Phe Gly Ser Asp
            100                 105                 110

Leu Asp Ala Ala Thr Gln Ala Lys Leu Asn Arg Gly Arg Arg Thr Val
        115                 120                 125

Glu Val Leu Lys Gln Pro Leu His Asn Pro Leu Pro Val Glu Lys Gln
    130                 135                 140

Val Leu Ile Leu Tyr Ala Leu Thr His Gly Phe Leu Asp Ser Val Pro
145                 150                 155                 160

Val Asp Gln Ile Leu Asp Phe Glu Gly Ala Leu Tyr Asp Tyr Phe Asp
                165                 170                 175

Ser His His Glu Asp Ile Phe Glu Thr Ile Arg Ser Thr Lys Asp Leu
            180                 185                 190

Pro Glu Glu Ala Val Leu Asn Glu Ala Ile Gln Ala Phe Lys Asp Gln
        195                 200                 205

Ser Glu Tyr Lys
        210

(2) INFORMATION FOR SEQ ID NO: 12:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO: 12:

Met Ala Gly Ser Leu Arg Glu Ile Lys Ala Lys Ile Ala Ser Ile Lys
 1               5                  10                  15

Gln Thr Ser His Ile Thr Gly Ala Met Gln Met Val Ser Ala Ser Lys
            20                  25                  30

Leu Thr Arg Ser Glu Gln Ala Ala Lys Asp Phe Gln Ile Tyr Ala Ser
        35                  40                  45

Lys Ile Arg Gln Ile Thr Thr Asp Leu Leu His Ser Glu Leu Val Asn
    50                  55                  60

Gly Ser Ser Asn Pro Met Leu Asp Ala Arg Pro Val Arg Lys Ser Gly
 65              70                  75                  80

Tyr Ile Val Ile Thr Ser Asp Lys Gly Leu Val Gly Gly Tyr Asn Ser
                85                  90                  95

Thr Ile Leu Lys Ala Val Leu Asp Met Ile Lys Arg Asp His Asp Ser
            100                 105                 110

Glu Asp Glu Tyr Ala Ile Ile Ser Ile Gly Gly Thr Gly Ser Asp Phe
        115                 120                 125

Phe Lys Ala Arg Asn Met Asn Val Ala Phe Glu Leu Arg Gly Leu Glu
```

```
                130                 135                 140
Asp Gln Pro Ser Phe Asp Gln Val Gly Glu Ile Ile Leu Lys Ala Val
145                 150                 155                 160

Gly Met Tyr Gln Asn Glu Leu Phe Asp Glu Leu Tyr Val Cys Tyr Asn
                165                 170                 175

His His Ile Asn Ser Leu Phe Cys Glu Val Cys Val Glu Lys Met Leu
                180                 185                 190

Pro Ile Ala Asp Phe Asp Pro Asn Glu Phe Glu Gly His Val Leu Thr
                195                 200                 205

Lys Phe Glu Leu Glu Pro Ser Cys Asp Thr Ile Leu Asp Gln Leu Leu
210                 215                 220

Pro Thr Ile Val Gly Glu Ser Phe Ile Tyr Gly Ala Ile Val Asp Ala
225                 230                 235                 240

Lys Thr Ala Glu His Ala Ala Gly Met Thr Ala Met Gln Thr Ala Thr
                245                 250                 255

Asp Asn Ala Lys Lys Ile Ile Asn Asp Leu Thr Ile Gln Tyr Asn Arg
                260                 265                 270

Ala Arg Gln Ala Ala Ile Thr Gln Glu Ile Thr Glu Ile Val Gly Gly
                275                 280                 285

Ala Ser Ala Leu Glu
            290

(2) INFORMATION FOR SEQ ID NO: 13:

(i) SEQUENCE CHARACTERISTICS:
        (A) LENGTH: 182 amino acids
        (B) TYPE: amino acid
        (D) TOPOLOGY: linear (ii) MOLECULE TYPE: protein (xi) SEQUENCE DESCRIPTION: SEQ ID NO: 13:

Met Ser Ser Gly Lys Ile Ala Gln Val Val Gly Pro Val Val Asp Val
1               5                   10                  15

Ala Phe Ala Thr Gly Asp Lys Leu Pro Glu Ile Asn Asn Ala Leu Val
                20                  25                  30

Val Tyr Thr Glu Lys Lys Ser Leu Arg Arg Met Val Leu Glu Val Ala
                35                  40                  45

Ser Leu Lys Leu Gly Glu Gly Val Val Arg Thr Ile Ala Met Glu Ser
            50                  55                  60

Thr Asp Gly Leu Thr Arg Gly Leu Glu Val Leu Asp Thr Gly Arg Pro
65                  70                  75                  80

Ile Ser Val Pro Val Gly Lys Glu Leu Leu Gly Arg Val Phe Asn Val
                85                  90                  95

Leu Gly Asp Thr Ile Asp Met Glu Ala Pro Phe Ala Asp Asp Ala Glu
                100                 105                 110

Arg Glu Pro Ile His Lys Lys Ala Pro Thr Phe Asp Glu Leu Ser Thr
                115                 120                 125

Ser Thr Glu Ile Leu Glu Thr Gly Ile Lys Val Ile Asp Leu Leu Ala
            130                 135                 140

Pro Tyr Leu Lys Gly Gly Lys Val Gly Leu Phe Gly Gly Ala Gly Val
145                 150                 155                 160

Gly Lys Ala Val Leu Ile Gln Glu Leu Asn His Asn Ile Ala Gln Glu
                165                 170                 175

His Gly Gly Ile Ser Val
            180
```

(2) INFORMATION FOR SEQ ID NO: 14:

(i) SEQUENCE CHARACTERISTICS:
        (A) LENGTH: 914 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: C-terminal (vi) ORIGINAL SOURCE:
        (A) ORGANISM: Phaffia rhodozyma (ix) FEATURE:
        (A) NAME/KEY: CDS
        (B) LOCATION:51..824
        (D) OTHER INFORMATION:/partial
            /codon_start= 51
            /product= "ATPase subunit, partial sequence"
            /gene= "ATP2"
            /standard_name= "beta subunit of the F1 portion of
            the F0F1 ATPase"
            /label= beta-subunit (xi) SEQUENCE DESCRIPTION: SEQ ID NO: 14:

```
GAATTCTCAA CCTTGAGGGT GACTCCAAGG TCGCTCTTGT CTTCGGACAG ATG AAC            56
                                                        Met Asn

GAG CCC CCG GGT GCT CGA GCC CGA GTC GCT TTG ACT GGT TTG ACC ATC          104
Glu Pro Pro Gly Ala Arg Ala Arg Val Ala Leu Thr Gly Leu Thr Ile
185                 190                 195                 200

GCC GAG TAC TTC CGA GAC GAG GAA GGA CAG GAT GTC TTG CTT TTC ATC          152
Ala Glu Tyr Phe Arg Asp Glu Glu Gly Gln Asp Val Leu Leu Phe Ile
                    205                 210                 215

GAC AAC ATT TTC CGA TTC ACC CAG GCC GGT TCT GAG GTG TCT GCC TTG          200
Asp Asn Ile Phe Arg Phe Thr Gln Ala Gly Ser Glu Val Ser Ala Leu
                220                 225                 230

CTT GGT CGA ATT CCC TCC GCC GTC GGA TAC CAG CCC ACT CTT TCC ACC          248
Leu Gly Arg Ile Pro Ser Ala Val Gly Tyr Gln Pro Thr Leu Ser Thr
            235                 240                 245

GAT ATG GGA GGT ATG CAG GAG CGA ATT ACC ACC ACC AAG AAG GGA TCC          296
Asp Met Gly Gly Met Gln Glu Arg Ile Thr Thr Thr Lys Lys Gly Ser
        250                 255                 260

ATC ACT TCC GTC CAG GCC GTC TAC GTG CCT GCT GAT GAT TTG ACC GAT          344
Ile Thr Ser Val Gln Ala Val Tyr Val Pro Ala Asp Asp Leu Thr Asp
265                 270                 275                 280

CCT GCC CCC GCC ACC ACC TTC GCC CAC TTG GAC GCC ACC ACT GTG TTG          392
Pro Ala Pro Ala Thr Thr Phe Ala His Leu Asp Ala Thr Thr Val Leu
                    285                 290                 295

TCT CGA GGT ATC GCT GAG TTG GGT ATC TAC CCC GCT GTC GAT CCC CTT          440
Ser Arg Gly Ile Ala Glu Leu Gly Ile Tyr Pro Ala Val Asp Pro Leu
                300                 305                 310

GAT TCT AAG TCC CGA ATG CTC GAC CCC CGA ATT GTC GGA CAG GAG CAC          488
Asp Ser Lys Ser Arg Met Leu Asp Pro Arg Ile Val Gly Gln Glu His
            315                 320                 325

TAC GAC ATC GCC ACC AAG ACC CAG AAG ATC CTC CAG GAC TAC AAG TCC          536
Tyr Asp Ile Ala Thr Lys Thr Gln Lys Ile Leu Gln Asp Tyr Lys Ser
        330                 335                 340

CTC CAG GAT ATC ATT GCC ATT CTT GGT ATG GAT GAG TTG TCT GAG GAG          584
Leu Gln Asp Ile Ile Ala Ile Leu Gly Met Asp Glu Leu Ser Glu Glu
```

```
345                 350                 355                 360
GAC AAG TTG ACC GTC GAG CGA GCC CGA AAG ATC CAG CGA TTC ATG TCG       632
Asp Lys Leu Thr Val Glu Arg Ala Arg Lys Ile Gln Arg Phe Met Ser
                365                 370                 375

CAG CCT TTC GCT GTC GCT CAG GTC TTC ACT GGT ATC GAG GGA AAG CTT       680
Gln Pro Phe Ala Val Ala Gln Val Phe Thr Gly Ile Glu Gly Lys Leu
            380                 385                 390

GTT CCC TTG AAG ACT ACT TTG GAG TCC TTT AAG GAG CTT CTT TCC GGA       728
Val Pro Leu Lys Thr Thr Leu Glu Ser Phe Lys Glu Leu Leu Ser Gly
        395                 400                 405

GCC TGC GAC CAC CTC CCT GAG TCT GCT TTC TAC ATG GTT GGT GAC ATC       776
Ala Cys Asp His Leu Pro Glu Ser Ala Phe Tyr Met Val Gly Asp Ile
    410                 415                 420

GCT GAT GTC AAG GCC AAG GCT GCT GCC CAG GCT AAG GAG TTG GCT GCT       824
Ala Asp Val Lys Ala Lys Ala Ala Ala Gln Ala Lys Glu Leu Ala Ala
425                 430                 435                 440

TAAGAGAAGA GTTGTCGAAT GTGTTTCGAG GTGTCAGAGT TGTCTTTTAT GAATGTTTCT     884

ATCTCCTTAA AAAAAAAAAA AAAAAAAAA                                      914

(2) INFORMATION FOR SEQ ID NO: 15:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO: 15:

Met Asn Glu Pro Pro Gly Ala Arg Ala Arg Val Ala Leu Thr Gly Leu
1               5                   10                  15

Thr Ile Ala Glu Tyr Phe Arg Asp Glu Glu Gly Gln Asp Val Leu Leu
                20                  25                  30

Phe Ile Asp Asn Ile Phe Arg Phe Thr Gln Ala Gly Ser Glu Val Ser
            35                  40                  45

Ala Leu Leu Gly Arg Ile Pro Ser Ala Val Gly Tyr Gln Pro Thr Leu
        50                  55                  60

Ser Thr Asp Met Gly Gly Met Gln Glu Arg Ile Thr Thr Lys Lys
65                  70                  75                  80

Gly Ser Ile Thr Ser Val Gln Ala Val Tyr Val Pro Ala Asp Asp Leu
                85                  90                  95

Thr Asp Pro Ala Pro Ala Thr Thr Phe Ala His Leu Asp Ala Thr Thr
            100                 105                 110

Val Leu Ser Arg Gly Ile Ala Glu Leu Gly Ile Tyr Pro Ala Val Asp
        115                 120                 125

Pro Leu Asp Ser Lys Ser Arg Met Leu Asp Pro Arg Ile Val Gly Gln
    130                 135                 140

Glu His Tyr Asp Ile Ala Thr Lys Thr Gln Lys Ile Leu Gln Asp Tyr
145                 150                 155                 160

Lys Ser Leu Gln Asp Ile Ile Ala Ile Leu Gly Met Asp Glu Leu Ser
                165                 170                 175

Glu Glu Asp Lys Leu Thr Val Glu Arg Ala Arg Lys Ile Gln Arg Phe
            180                 185                 190

Met Ser Gln Pro Phe Ala Val Ala Gln Val Phe Thr Gly Ile Glu Gly
        195                 200                 205

Lys Leu Val Pro Leu Lys Thr Thr Leu Glu Ser Phe Lys Glu Leu Leu
    210                 215                 220
```

```
Ser Gly Ala Cys Asp His Leu Pro Glu Ser Ala Phe Tyr Met Val Gly
225                 230                 235                 240

Asp Ile Ala Asp Val Lys Ala Lys Ala Ala Gln Ala Lys Glu Leu
                245                 250                 255

Ala Ala (2) INFORMATION FOR SEQ ID NO: 16:

(i) SEQUENCE CHARACTERISTICS:
        (A) LENGTH: 375 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Trichoderma reesei (ix) FEATURE:
         (A) NAME/KEY: CDS
         (B) LOCATION:50..361
         (D) OTHER INFORMATION:/partial
             /codon_start= 50
             /product= "ATPase subunit, partial sequence"
             /gene= "ATP2"
             /standard_name= "beta subunit of F1 portion of the
             F0F1 ATPase"
             /label= beta-subunit (xi) SEQUENCE DESCRIPTION: SEQ ID NO: 16:

TACTCGAAGA ATTCGGCACG AGGCTGATTG CTCTCGGTCA TCTGCCAAG ATG TTC           55
                                                      Met Phe
                                                          260

AAG AGC GGC GTT TCG TCC CTC GCC AGG GCT GCC CGC CCA TCA ATT ACC       103
Lys Ser Gly Val Ser Ser Leu Ala Arg Ala Ala Arg Pro Ser Ile Thr
                265                 270                 275

GCT CGA CGA GCT ATC CGA CCA GCC TTC CCT CGA ACC CCC CTC GCG AGG       151
Ala Arg Arg Ala Ile Arg Pro Ala Phe Pro Arg Thr Pro Leu Ala Arg
                280                 285                 290

CTT GCC AGC ACC CAG AGC GTC GGA GAT GGC AAG ATC CAC CAG GTC ATT       199
Leu Ala Ser Thr Gln Ser Val Gly Asp Gly Lys Ile His Gln Val Ile
                295                 300                 305

GGT GCC GTC GTC GAC GTC AAG TTC GAC ACC GCC AAG CTG CCT CCT ATC       247
Gly Ala Val Val Asp Val Lys Phe Asp Thr Ala Lys Leu Pro Pro Ile
    310                 315                 320

CTG AAC GCC CTG GAG ACC ACC AAC AAC AAC CAG AAG CTG GTC CTC GAG       295
Leu Asn Ala Leu Glu Thr Thr Asn Asn Asn Gln Lys Leu Val Leu Glu
325                 330                 335                 340

GTG GCT CAA CAC TTG GGC GAG AAT GTC GTT CGC TGC ATT GCC ATG GAC       343
Val Ala Gln His Leu Gly Glu Asn Val Val Arg Cys Ile Ala Met Asp
                345                 350                 355

GGA TCC GAG GGT CTC GTC GTGGTTCCAA GGCA                               375
Gly Ser Glu Gly Leu Val
                360

(2) INFORMATION FOR SEQ ID NO: 17:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO: 17:
```

-continued

```
Met Phe Lys Ser Gly Val Ser Ser Leu Ala Arg Ala Ala Arg Pro Ser
 1               5                  10                  15

Ile Thr Ala Arg Arg Ala Ile Arg Pro Ala Phe Pro Arg Thr Pro Leu
            20                  25                  30

Ala Arg Leu Ala Ser Thr Gln Ser Val Gly Asp Gly Lys Ile His Gln
            35                  40                  45

Val Ile Gly Ala Val Val Asp Val Lys Phe Asp Thr Ala Lys Leu Pro
     50                  55                  60

Pro Ile Leu Asn Ala Leu Glu Thr Thr Asn Asn Asn Gln Lys Leu Val
 65                  70                  75                  80

Leu Glu Val Ala Gln His Leu Gly Glu Asn Val Val Arg Cys Ile Ala
                85                  90                  95

Met Asp Gly Ser Glu Gly Leu Val
                100
```

METHOD OF IMPROVING THE PRODUCTION OF BIOMASS OR A DESIRED PRODUCT FROM A CELL

This is a continuation of U.S. patent application Ser. No. 10/310,630, filed Dec. 5, 2002 and now abandoned, which is a divisional of U.S. patent application Ser. No. 09/254,504, filed Aug. 4, 1999, now U.S. Pat. No. 6,511,836. U.S. patent application Ser. No. 09/254,504 is a U.S. National Phase Application under 35 U.S.C. §371 of International Patent Application Serial No. PCT/DK97/00373, filed Sep. 8, 1997, and which claims the benefit of Denmark Patent Application Serial No. 0963/96, filed Sep. 6, 1996.

This invention relates to a method of improving the production of biomass or a desired product from a cell by inducing conversion of ATP to ADP without primary effects on other cellular metabolites or functions. The invention also relates to a method of optimizing the production of biomass or a desired product from a cell utilizing this first method. The desired product may for example be lactic acid produced by lactic acid bacteria and ethanol or carbondioxide produced by yeast.

BACKGROUND OF THE INVENTION

A wide range of microorganisms are used for the production of various organic compounds and heterologous proteins. One example hereof is the production of lactic acid and other organic compounds by the lactic acid group of bacteria, which results in the acidification and flavouring of dairy products, better known as cheese and yougurt production.

From the microorganism's point of view, the organic compounds which are excreted from the cells are often merely the by-product of a process that is vital to the cells: the production of various forms of free energy (ATP, NAD(P)H, membrane potential, etc.). Therefore, although many of the microorganisms which are being employed in these processes are reasonably well suited for the purpose, there is still a great potential for optimizing the productivity of these organisms when looking from the bioreactor point of vue. Likewise, the production of heterologous proteins by a microorganism is not what the organism was adapted for and also here there is a potential for optimization.

Often when microorganisms are engineered for the purpose of optimizing an industrial production process, the reactions leading to the desired product will affect the delicate balance of co-factors involved in the energy metabolism of the cell. For instance if the glycolytic reactions producing lactate from sugar were somehow to be enhanced (e.g. by overexpressing the glycolytic enzymes) this would automatically lead to the convertion of ADP to ATP. The ratio between the concentrations of ATP and ADP is usually quite high in the growing cell ([ATP]/[ADP]>10), and when the ratio [ATP]/[ADP] changes, the sum of [ATP] and [ADP] still remains virtually constant. Therefore, if in the example above, the enhanced production of ATP changes the [ATP]/[ADP] ratio from 10 to say 30, this will only marginally affect the concentration of ATP. The ADP concentration however will change by a factor of three. The cells will then hardly feel the surplus of ATP but the ADP pool in the cells may be depleted to such an extent that reactions in which ADP is a co-factor or allosteric regulator will be suppressed by the lack of ADP. The result may be that the total flux through the pathway (here through glycolysis) is only marginally increased. In the future, this situation is likely to occur more frequently, as the productivity of bioreactors are optimized by other means, and in these cases, it will be even more important (compared to the normal cell) to regenerate the ADP from ATP, in order to further increase the productivity.

Previously, attempts have been made to decrease the intracellular ATP concentration in yeast, employing sets of reactions which together form futile cycles, see EP patent No. 245 481. Often, the first reaction of a futile cycle is part of the regular metabolic network of the cell, for instance the phosphorylation of a glycolytic intermediate, coupled to the utilisation of ATP. The second reaction, which may also sometimes be part of the metabolic network, then dephosphorylates the glycolytic intermediate without regenerating the ATP that was consumed in the first process, the overall effect being that a high energy phosphate bond is consumed. The limited success that this strategy has had so far, is probably due to the fact that it is impossible to obtain a significant futile flux without decreasing the concentration of the phosphorylated intermediate, thereby disturbing the cellular function and ultimately the growth. In addition, when the approach is to decrease the concentration of a glycolytic intermediate, this will effectively remove the substrate for the remaining part of the glycolysis, which will often result in a decreased flux through this pathway, rather than the desired increased flux.

Other strategies have been to use chemicals such as dinitrophosphate to stimulate the activity of the plasma membrane $H^+$-ATPase by the addition of uncouplers of the membrane potential, or to genetically express the enzyme acid phosphatase in the cytoplasm, an enzyme that will remove phosphate groups from organic metabolites and proteins. However, both of these approaches suffer from the same inherent problem: they are unspecific and a range of cellular reactions/concentrations may be affected. For instance, the acid phosphatase will remove phosphate groups from essential metabolites and proteins, thus disturbing various metabolic fluxes and metabolic regulation. The uncoupling of the plasma membrane $H^+$-ATPase will disturb the intracellular pH in addition to the gradient of numerous ions across the cytoplasmic membrane. Besides, the addition of chemicals such as dinitrophosphate is undesirable for most purposes.

SUMMARY OF THE INVENTION

The idea of the invention is to use a highly specific and clean way to increase the intracellular level of ADP, which does not suffer from the limitations described above: to express in a well-controlled manner an enzyme that has ATP-hydrolytic activity in the living cell without producing other products and without coupling this activity to energy conservation. Such an enzymatic activity is of course not likely to be found in a normal cell, because the cell would then loose some of its vital energy reservoir.

Accordingly the present invention provides a method of improving the production of biomass or a desired product from a cell, the method being characterized by expressing an uncoupled ATPase activity in said cell to induce conversion of ATP to ADP without primary effects on other cellular metabolites or functions, and incubating the cell with a suitable substrate to produce said biomass or product.

One of the normal enzymes that comes closest to the ideal ATP-hydrolyzing enzyme, is the membrane bound $H^+$-ATPase. This huge enzyme complex consists of two parts, the membrane integral part ($F_0$) and the cytoplasmic part ($F_1$).

Together the two parts couples the hydrolysis of ATP to ADP and inorganic phosphate ($P_i$), to translocation of protons accross the cytoplasmic membrane, or vice versa, using the proton gradient to drive ATP synthesis from ADP and $P_i$.

The method of the invention is conveniently carried out by expressing in said cell the soluble part ($F_1$) of the membrane bound ($F_0F_1$ type) $H^+$-ATPase or a portion of the $F_1$ exhibiting ATPase activity.

The membrane bound $H^+$-ATPase complex is found in similar form in prokaryotic as well as eukaryotic organisms, and thus $F_1$ and portions thereof expressing ATPase activity can be expressed in both prokaryotic and eukaryotic cells.

The organism from which the F1 ATPase or portions thereof is derived, or in which the F1 ATPase or portions thereof is expressed, may be selected from prokaryotes and eukaryotes, in particular from bacteria and eukaryotic microorganisms such as yeasts, other fungi and cell lines of higher organisms, in particular bakers and brewers yeast.

A particularly interesting group of prokaryotes to which the method according to the invention can be implemented, i.a. in the dairy industry, are lactic acid bacteria of the genera *Lactococcus, Streptococcus, Enterococcus, Lactobacillus* and *Leuconostoc*, in particular strains of the species *Lactococcus lactis* and *Streptococcus thermophilus*. Other interesting prokaryotes are bacteria belonging to the genera *Escherichia, Zymomonas, Bacillus* and *Pseudomonas*, in particular the species *Escherichia coli, Zymomonas mobilis, Bacillus subtilis* and *Pseudomonas putida*.

In an expedient manner of carrying out the method according to the invention the cell is transformed or transfected with an expression vector including DNA encoding $F_1$ or a portion thereof exhibiting ATPase activity under the control of a promoter functioning in said cell, and said DNA is expressed in the cell. Said DNA encoding $F_1$ or a portion thereof may be derived from a prokaryotic or a eukaryotic organism, and it may be either homologous or heterologous to said cell.

The $F_1$ part of the bacterial $H^+$-ATPase complex consists of several subunits that together are responsible for catalyzing ATP hydrolysis: the β-subunit is thought to carry the actual hydrolytic site for ATP hydrolysis, but in vitro ATPase activity requires that the β-subunit forms a complex together with the α- and γ-subunit ($\alpha_3\gamma\beta_3$). The activity of this complex is modulated by the ε-subunit, so that the in vitro activity of the $\alpha_3\gamma\beta_3\epsilon$ complex is five fold less than the $\alpha_3\gamma\beta_3$ complex.

In a specific embodiment of the method according to the invention said DNA encoding $F_1$ or a catalytic active portion thereof, is derived from *Escherichia coli, Streptococcus thermophilus* or *Lactococcus lactis* and is selected from the group consisting of the gene encoding the $F_1$ subunit β or a catalytically active portion thereof and various combinations of said gene or portion with the genes encoding the $F_1$ subunits β, α, γ and ε or catalytically active portions thereof.

In particular said DNA encoding $F_1$ or a portion thereof may be selected from the group consisting of the *Escherichia coli, Streptococcus thermophilus* and *Lactococcus lactis* genes atpHAGDC (coding for subunits δ, α, γ, β, ε), atpAGDC (coding for subunits α, γ, β, ε), atpAGD (coding for subunits α, γ, β), atpDC (coding for subunits β, ε) and atpD (coding for subunit β alone).

Particularly interesting eukaryotes are the yeasts *Saccharomyces cerevisiae, Phaffia rhodozyma* or *Trichoderma reesei*, and the DNA encoding $F_1$ or a portion thereof may be derived from such organisms and is selected from the group consisting of the gene encoding the $F_1$ subunit β or a portion thereof and various combinations of said gene or portion with the genes encoding the other $F_1$ subunits or portions thereof.

Vectors including DNA encoding the soluble part ($F_1$) of the membrane bound ($F_0F_1$ type) $H^+$-ATPase or a portion of $F_1$ exhibiting ATPase activity, derived from the lactic acid bacteria *Lactococcus lactis* and *Streptococcus thermophilus* and from the yeasts *Saccharomyces cerevisiae, Phaffia rhodozyma* or *Trichoderma reesei* are also comprised by the invention as well as expression vectors including such DNA under the control of a promoter capable of directing the expression of said DNA in a prokaryotic or eukaryotic cell.

Specific vectors according to the invention are plasmids including DNA encoding the soluble part ($F_1$) of the membrane bound ($F_0F_1$ type) $H^+$-ATPase or a portion of $F_1$ exhibiting ATPase activity, said DNA being derived from *Lactococcus lactis* subsp. *cremoris* (SEQ ID No. 1), *Lactococcus lactis* subsp. *lactis* (SEQ ID No. 6), *Streptococcus thermophilus* (SEQ ID No. 10), *Phaffia rhodozyma* (SEQ ID No. 14), and *Trichoderma reesei* (SEQ ID No. 16).

Further, the invention provides a method of optimizing the formation of biomass or a desired product by a cell, the method being characterized by expressing different levels of uncoupled ATPase activity in the cell, incubating the cell on a suitable substrate, measuring the conversion rate of substrate into biomass or the desired product at each level of ATPase expression, and choosing a level of ATPase expression at which the conversion rate is optimized.

Often, but not always, the optimization of a given product flux produced by a cell will entail the attainment of either maximum or minimum conversion rate of a substrate.

In an expedient manner of practicing this method of the invention a number of specimens of said cell are transformed or transfected with their respective expression vector each including DNA encoding a different portion of the cytoplasmic part ($F_1$) of the membrane bound ($F_0F_1$ type) $H^+$-ATPase up to and including the entire $F_1$, each portion exhibiting ATPase activity, said DNA in each expression vector being under the control of a promoter functioning in said cell, incubating each cell specimen on a suitable substrate, measuring the conversion rate of substrate into biomass or the desired product in each specimen, and choosing a specimen yielding an optimal conversion rate. In a particular embodiment of this manner, which is especially suited for scientific studies, the promoter in each expression vector is an inducible promoter, and each cell specimen is grown at different concentrations of inducer in order to fine-tune the optimal conversion rate.

In a preferred manner of practicing the above method of optimizing the performance of a cell a number of specimens of said cell are transformed or transfected with their respective expression vector including DNA encoding a portion of the cytoplasmic part ($F_1$) of the membrane bound ($F_0F_1$ type) $H^+$-ATPase up to and including the entire $F_1$, said portion exhibiting ATPase activity, said DNA in the respective expression vectors being under the control of each of a series of promoters covering a broad range of promoter activities and functioning in said cell, incubating each cell specimen on a suitable substrate, measuring the conversion rate of substrate into biomass or the desired product by each specimen, and choosing a specimen yielding an optimal conversion rate. In a more preferred embodiment of this manner, which is well suited to establish an optimal production strain, the respective expression vectors include DNA encoding different such portions of $F_1$ up to and including the entire $F_1$, each DNA in respective expression vectors being under the control of each of a series of promoters covering a broad range of promoter activities and functioning in said cell.

Also in this method of the invention the DNA encoding a portion of $F_1$ up to and including the entire $F_1$ may be derived from a prokaryotic or a eukaryotic organism, and it may be either homologous or heterologous to said organism. The specific DNAs mentioned above may also conveniently be employed in this method.

DETAILED DESCRIPTION OF THE INVENTION

Figure 1:
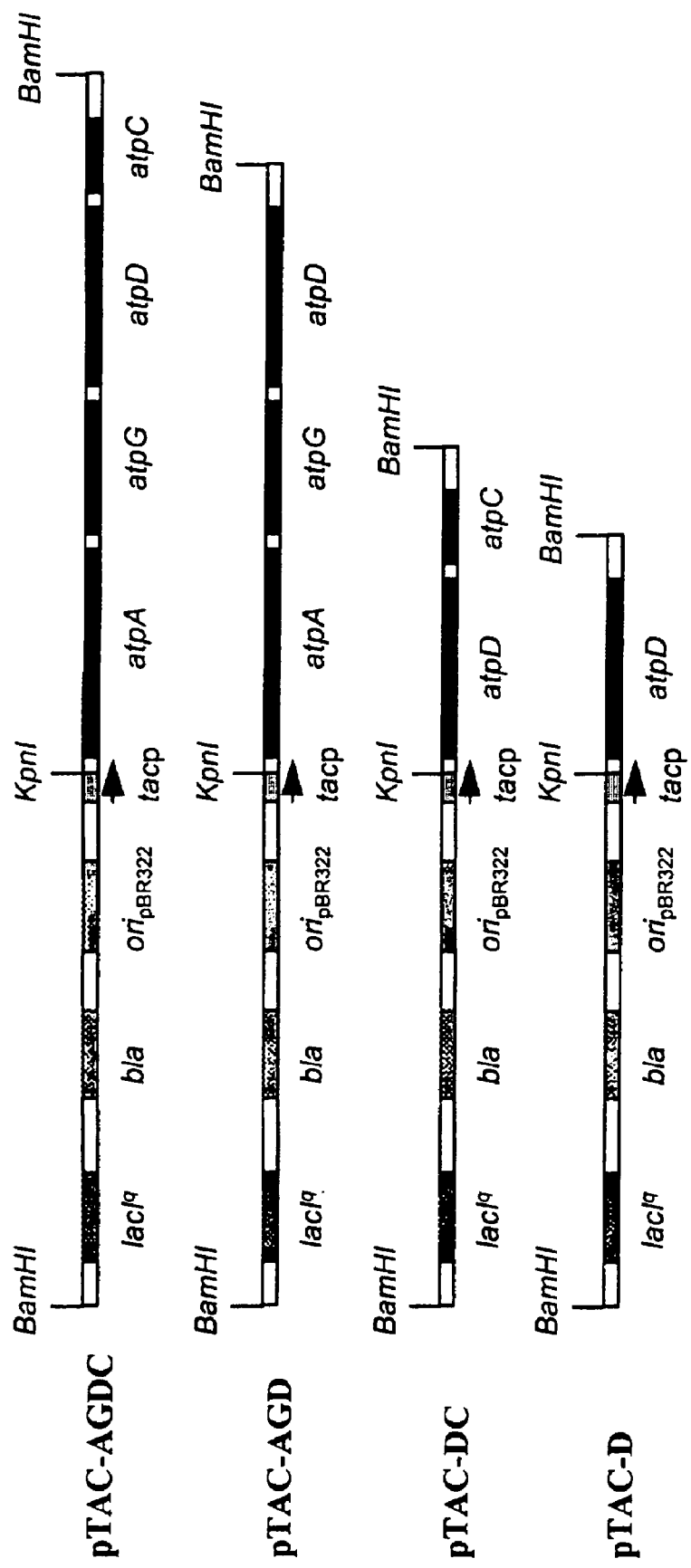
FIG. 1. A linear representation of the plasmids constructed for modulating the cellular [ATP]/[ADP] ratio in E. coli (not drawn to scale).

Many biosynthetic reactions in the living cell (anabolism), require an input of free energy (ATP), which is generated through a series of degrading reactions (catabolism). In the aerobic cell, there are two routes for ATP synthesis: 1) substrate level phosphorylation, where an energy rich phosphoryl group is transferred directly from a high energy intermediate metabolite to ADP, and 2) oxidative phosphorylation, where the free energy is first transformed into redox free energy by oxidizing the energy source, then into a proton gradient by respiration and finally the proton gradient is used by the $H^+$-ATPase to drive ATP synthesis from ADP and inorganic phosphate. In other cases, e.g. anaerobic growth, there is only the first route, substrate level phosphorylation, that can be used for ATP synthesis. An example hereof is the homolactic LAB, where lactose is converted through the glycolytic pathway to lactic acid, which is excreted from the cells and thereby lowers the pH of the growth medium (usually milk products). With respect to ATP generation, homolactic fermentation is a very inefficient process, and only four moles of ATP are produced from 1 mole of lactose through substrate level phosphorylation.

The anabolic (ATP consuming) and catabolic (ATP producing) fluxes are normally well balanced in the living cell, and therefore, in the wild-type cell under normal growth conditions, the catabolic fluxes will be proportional to the anabolic fluxes. If a reaction is introduced that for instance hydrolyzes ATP in the cell and thereby lowers the cellular energy state (i.e. the [ATP]/[ADP] ratio), then either catabolism should increase or anabolism (growth) should decrease in order to make the consumption rate equal the production rate again. Which of these two scenarios will take place depends on whether, initially, the growth rate of the cell is limited through anabolism or through catabolism, i.e. whether there is a surplus or a shortage of energy in the cell to begin with. If there is a shortage of energy, then the rate of the anabolic reactions is limited by catabolism and these reactions will be sensitive to changes in the cellular energy state. Introduction of an ATP-hydrolyzing reaction is then most likely to affect the growth rate of the cells. On the other hand, if there is a surplus of energy, then the growth rate will be limited mainly by the anabolic reactions; the rate of anabolism will be insensitive to a decrease in the energy state, but the catabolic rate may increase due to a decrease in product inhibition at lower [ATP]/[ADP] ratio.

In vitro, the $F_1$ part of the $H^+$-ATPase complex has been shown to have ATPase actitity, see above. But so far nobody has managed to use the $F_1$ complex to stimulate the glycolytic flux, or even to show that the $F_1$ complex can hydrolyze ATP in intact cells. Indeed, when we first tried to overexpress the F1 complex, consisting of the genes for the subunits $\alpha$, $\gamma$, $\beta$ and $\epsilon$, this had virtually no effect on the growth of E. coli, even when the genes were transcribed from the maximally induced tac promoter and on a very high copy number vector (derived from pUC18). One skilled in the art of gene expression in E. coli will appreciate that this combination is one of the most efficient expression systems that exists for this organism.

We then decided to try to express different combinations of subunits of the F1 complex, in order to see if other combinations of subunits would be more powerful. Plasmids were constructed containing various combinations of the genes encoding the $F_1$ part of the bacterial $F_1F_0$-ATPase complex from E. coli. The genes were expressed, either from an inducible (lac-type) promoter at various concentrations of inducer or from a series of constitutive promoters of varying promoter activity. These plasmids should express various levels of ATPase activity when introduced into the bacterial cell. Depending on which $F_1$ genes are present on the plasmid and the strength of the promoter which is used to drive the expression, we observed various degrees of inhibition of the growth of the cells harbouring these plasmids. Surprisingly, the beta subunit alone and in combination with the epsilon subunit turned out to be far more active in vivo than the entire F1 complex.

The objective of this work was to affect the energy state of the cells, as reflected in the ratio [ATP]/[ADP]. We therefore measured the intracellular concentration of ATP and ADP in growing cells expressing various activities of $F_1$-ATPase. Indeed the ATP concentration decreased slightly with increasing ATPase activity and the ADP concentration increased, and therefore the [ATP]/[ADP] ratio decreased (the effect on the ATP concentration was less than the effect on the ADP concentration as expected, see above). We also calculated the glycolytic flux through the cells with various levels of ATPase activity. We found that the flux through the glycolytic pathway was first stimulated with increasing expression of ATPase activity, until a certain (optimal) ATPase activity which gave maximal glycolytic flux. Further increase of ATPase expression resulted in a lower glycolytic flux, due to a secondary effect of the ATPase activity on the growth of the cells. This emphasizes the need for optimization of gene expression rather than merely overexpressing the genes.

EXAMPLE 1

ATP Hydrolysis and Enhanced Glycolytic Flux in Escherichia coli, using an Inducible Promoter Restriction enzymes, T4 DNA polymerase, calf intestine phosphatase (CIP) were obtained from Pharmacia.

Procedures for DNA isolation, cutting with restriction enzymes, filling in sticky DNA ends with T4 DNA polymerase in the presence of dATP, dCTP, dGTP and dTTP, treatment with calf intestine phophatase to remove phosphate groups from 5' DNA ends and ligation of DNA fragments are carried out by standard methods as described by Maniatis et al., 1982.

Extraction and Measurement of ATP and ADP 0.9 ml of cell culture was mixed with 0.9 ml of (80° C.) phenol (equilibrated with 10 mM Tris, 1 mM EDTA pH=8) and immediately vortexed vigorously for 10 seconds. After 1 hour at room temperature the sample was vortexed again for 10 seconds and the two phases were separated by centrifugation at 14000 rpm for 15 minutes, and then residual phenol in the water phase was removed by extraction with 1 volume of chloroform. ATP and ADP concentrations were then measured, using a luciferin-luciferase ATP monitoring kit (obtained from and used as recommended by LKB, except that 3 mM of phosphoenol-pyruvate was added). [ATP] was measured first. Subsequently the ADP in the same sample was converted to ATP by adding pyruvate kinase, and [ADP] was recorded as the concomitant increase in luminescence.

Construction of Plasmids Carrying Combinations of the *E. coli* atp Genes

The following combinations of *E. coli* genes coding for $F_1$ subunits were chosen for expressing ATPase activity in *E. coli*: 1. atpAGDC (subunits $\alpha$, $\gamma$, $\beta$, $\epsilon$), 2. atpAGD (subunits $\alpha$, $\gamma$, $\beta$), 3. atpDC (subunits $\beta$, $\epsilon$), and 4. atpD (subunit $\beta$ alone).

Cloning of Fragments Carrying atp Genes Onto pUC19

The plasmid pBJC917 (von Meyenburg, K., et al., 1984) which carries the entire atp operon was cut with
1) the restriction enzyme DraIII, and a 5009 bp DNA fragment containing the atpAGDC genes was isolated;
2) the restriction enzymes DraIII and Tth111I, and a 4106 bp DNA fragment containing the atpAGD genes was isolated;
3) the restriction enzymes DraIII and SacII, and a 2364 bp DNA fragment containing the atpDC genes was isolated;
4) the restriction enzymes AvaI and Tth111I, and a 1472 bp DNA fragment containing the atpD gene was isolated.

In all four cases the fragments were then treated with T4 DNA polymerase to create blunt ends, and subsequently the fragments were ligated into the cloning vector pUC19 (Yanisch-Perron et al., 1985) which had been cut with SmaI and treated with CIP.

The four ligation mixtures were transformed into the *E. coli* strain JM105 (Yanisch-Perron et al., 1985), and the transformation mixtures were plated on LB (Luria-Bertani broth; Maniatis et al., 1982) plates containing 100 µg/ml ampicillin and 75 µg/ml 5-bromo-4-chloro-3-indolyl-β-Dgalactoside (X-gal). In this strain background (JM105), plasmids formed by religation of pUC19 will give blue colonies, whereas plasmids that carry foreign DNA fragments inserted into the SmaI site of pUC19, will give white colonies. A number of white colonies from the four transformations were therefore picked for further analysis: plasmid DNA was isolated and analysed by cutting with various restriction enzymes. Clones were identified from each of the four series which had the desired fragment inserted into the SmaI site of pUC19, and in the proper orientation. These four plasmids were named, respectively: pATP-AGDC, pATP-AGD, pATP-DC and pATP-D, with reference to the specific atp genes carried by the plasmid.

Cloning Combinations of the atp Genes Under the Control of an Inducible (tac) Promoter In order to be able to control the expression of the ATPase activity, we selected the expression vector pTTQ18 (Starck, 1987). This vector is a derivative of pUC18 (Yanisch-Perron et al., 1985), which carries a tac promoter and the lactose repressor gene, lacI. Immediately downstream of the tac promoter is a multiple cloning site (MCS; the polylinker from pUC18) in which genes can be inserted to be expressed from the tac promoter. The tac promoter is of the lac-type, i.e. repressed by the lactose repressor and inducible with isopropyl-β-D-thiogalactoside (IPTG).

The four plasmids, pATP-AGDC, pATP-AGD, pATP-DC and pATP-D were cut with KpnI and XbaI, which gave the four DNA fragments, 5023, 4120, 2378 and 1486 respectively. After purification, the fragments were ligated into the cloning vector, pTTQ18, which had also been cut with KpnI and XbaI (see FIG. 1). The ligation mixtures were transformed into *E. coli* K-12 MC1000 (Casabadan and Cohen, 1980), and the transformation mixtures were plated on LB plates containing 100 µg/ml ampicillin. A number of colonies from the four transformations were therefore picked for further analysis: plasmid DNA was isolated and analysed by cutting with various restriction enzymes. Clones were identified from each of the four series which had the desired fragment inserted into the MCS of pTTQ18 in the proper orientation. These four plasmids were named, respectively: pTAC-AGDC, pTAC-AGD, pTAC-DC and pTAC-D, with reference to the specific atp genes carried by these plasmid and the tac promoter used for their expression. For the purpose of subsequent physiological studies, the plasmids were transformed into the *E. coli* K-12 strain LM3118, which is used routinely for physiological experiments in this laboratory. The corresponding names for the LM3118 strain carrying these four plasmids are PJ4332, PJ4333, PJ4335 and PJ4334, respectively.

Effect of Induction of ATPase Activity on the Growth of *E. coli* on Plates

The strains containing the four plasmids were streaked on LB plates containing ampicillin (100 µg/ml) and 1 mM of IPTG which should give maximum expression from the tac promoter. Table I shows how the four strains responded: the strain carrying plasmid pATP-AGDC, which contains the genes for the four subunits, $\alpha$, $\gamma$, $\beta$ and $\epsilon$, was only very slightly affected in growth, even in the presence of 1 mM IPTG. The other three plasmids, pTAC-AGD, pTAC-DC and pTAC-D caused severe growth inhibition in the presence of 1 mM IPTG, where colonies were no longer visible. With intermediate concentrations of IPTG, 0.01 mM and 0.1 mM, the plasmids affected the growth of their host cells to different extents: pTAC-AGD was the most active, giving rise to a strong inhibition of growth already with 0.01 mM IPTG, a concentration which gave only a slight inhibition with the plasmid pTAC-DC and no inhibition of the strain with pTAC-D. With 0.1 mM IPTG, colonies were hardly visible for the strain that carried the pTAC-AGD, the plasmid pTAC-DC caused strong growth inhibition, whereas the effect of pTAC-D was significant but small.

TABLE I

| Strain | Plasmid | –IPTG | 0.01 mM IPTG | 0.1 mM IPTG | 1 mM IPTG |
|---|---|---|---|---|---|
| PJ4332 | pTAC-AGDC | ++++ | ++++ | ++++ | +++ |
| PJ4333 | pTAC-AGD | ++++ | ++ | + | – |
| PJ4335 | pTAC-DC | ++++ | +++ | + | – |
| PJ4334 | pTAC-D | ++++ | ++++ | ++ | – |

++++ = normal colony size;
+++ = slight inhibition;
++ = ½ normal size;
+ = 1/10 normal size;
– = no growth The effect of ATPase expression from the four plasmids above was also studied in the *E. coli* mutant LM3115, in which the entire atp operon on the chromosome is deleted, but which grows with almost wild-type growth rate on LB medium. With this strain transformed with the four plasmids we observed a similar pattern of growth inhibition on LB plates as a function of IPTG concentration. This shows that the effect of ATPase expression was independent of the presence of the normal atp operon.

Figure 2:
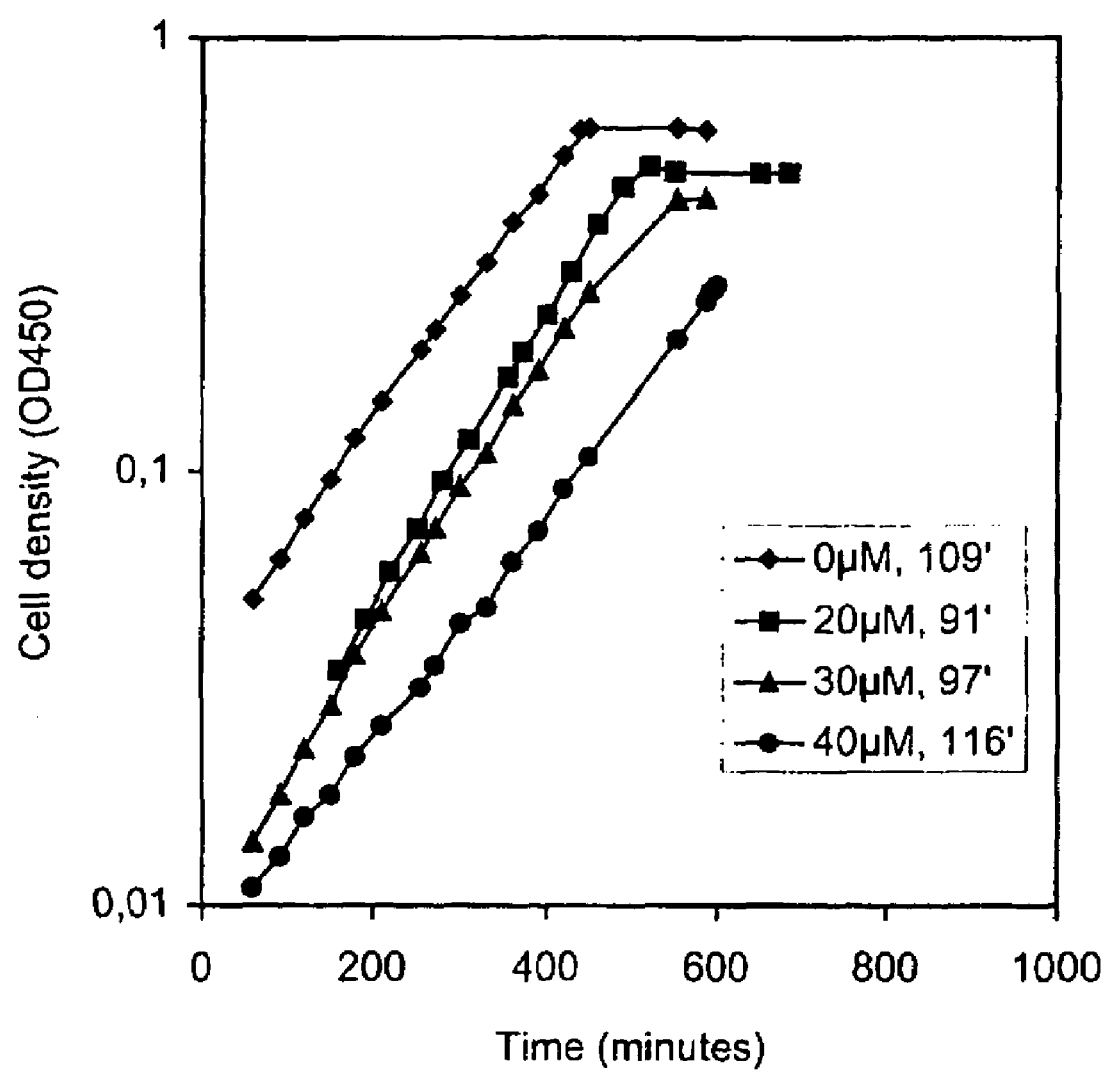
FIG. 2. Effect of induction of $F_1$-ATPase activity on the growth of E. coli in batch culture. Cells were grown for more than 10 generations in minimal medium supplemented with glucose (0.4 g/l), ampicillin (0.1 g/l) and the indicated concentration of inducer, IPTG.

Effect of Induction of ATPase Activity on the Growth of *E. coli* in Liquid Cultures The effect of induction of ATPase was also studied with cells grown in liquid cultures. For this purpose we chose the strain PJ4333, carrying the plasmid PTAC-AGD, because this plasmid appears to be the most active with respect to the inhibitory effect on the of growth of *E. coli*. FIG. 2 shows the growth of PJ4333 in minimal medium supplemented with a limiting concentration of glucose (0.4 g/l) and ampicillin (0.1 g/l), without IPTG and in the presence of increasing concentrations of IPTG. We observed that the growth rate of the strain was practically constant (within some 10%) with increasing amounts of IPTG up to about 30 μM. At higher than 40 μM IPTG, the growth of the cells were slightly inhibited, in accordance with the experiments on plates, see above.

However, what was affected was the final density of cells that one obtains from the limited amount of glucose that was included in each culture: The more ATPase that is expressed in the cells, the lower the yield of cell mass. Apparently, the cells become less economic with respect to converting the glucose into biomass, or in other words they consume more glucose per cell synthesized. If this is due to the expression of ATPase activity, then we would expect to see an effect hereof on the energy state of the cells. We therefore measured the concentrations of ATP and ADP in the cells growing with different expression levels of ATPase activity.

Figure 3:
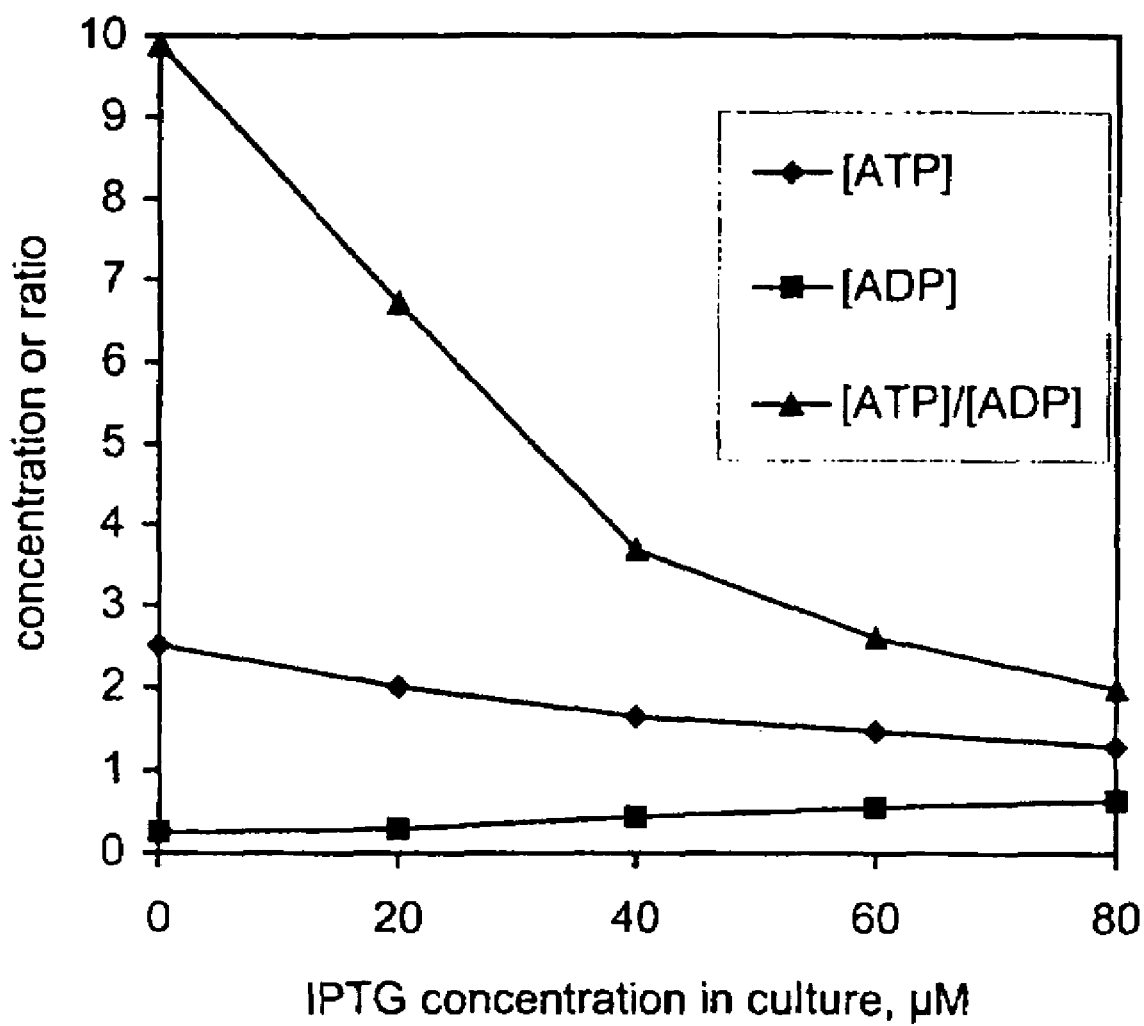
FIG. 3. Effect of ATPase expression on the intracellular concentration of ATP and ADP (concentration in arbitrary units), and on the ratio [ATP]/[ADP].

Indeed, the intracellular ATP concentration decreased gradually and the ADP concentration increased, with increased expression of ATPase; therefore the [ATP]/[ADP] ratio decreased with increased expression of ATPase, which imply that the increased glucose consumption is the result of increased ATP convertion to ADP, see FIG. 3. The actual flux of glucose through the cells ($J_{gluc}$, mmol glucose/g cell dry weight/hour) is also interesting, because this value tells us whether the performance of the cell increased as the ATPase activity increased. $J_{gluc}$ can be calculated from the yield, Y (g cell dry weight/mol glucose) and the specific growth rate of the culture, μ (1/hours):

$$J_{gluc} = \mu / Y$$

Figure 4:
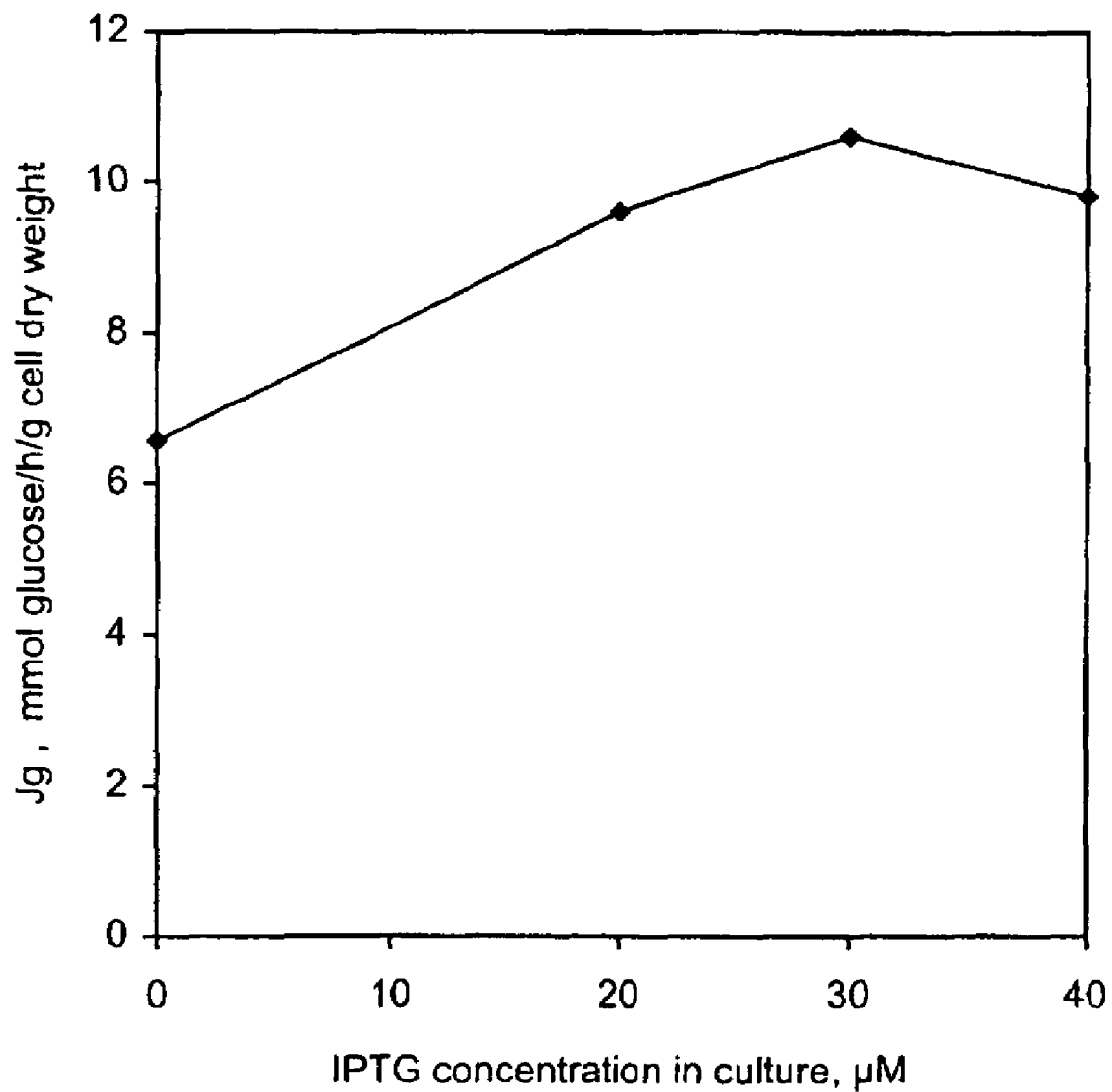
FIG. 4 Effect of increased ATPase expression on the glycolytic flux.

FIG. 4 shows how the flux of glucose changed as the activity of ATPase increased: the glycolytic flux increased gradually as the ATPase expression increased, until a maximum was reached (at 30 μM IPTG). Further increase of ATPase expression had a slightly negative effect on the glucose flux. This was probably because the energy state of the cells became so low that this had a negative effect on some anabolic reactions, since the growth rate was lower for the culture that was grown in the presence of 40 μM IPTG.

The expression of subunits of the $F_1$ part of the bacterial $H^+$-ATPase lowers the energy state of the bacterial cell. This is due to hydrolysis of ATP into ADP and $P_i$. The expression of ATPase activity does not affect the growth rate of *E. coli* much at low levels of expression, but the efficiency by which the substrate is converted into biomass was strongly reduced. Under the set of conditions used here, the expression of ATPase activity has a stimulatory effect on the rate by which the cells consumes the exogenous glucose.

EXAMPLE 2

Expression of $F_1$-ATPase Activity from Constitutive Promoters in *E. coli*

In example 1 we used a lac-type promoter system to modulate the expression of the $F_1$ ATPase subunits in *E. coli*. However, for the optimization of gene expression for instance in industrial bioreactors or for the use in fermented food products, the use of lac type promoters is not always feasible. In this example we illustate the optimization of $F_1$-ATPase expression in *E. coli*, using a series of constitutive promoters of different strength, to control the expression of the atpAGD genes which here originates from *E. coli*. The constitutive promoters (CP promoters) were selected from a library of artificial promoters which had previously been cloned onto a shuttle vector for *E. coli* and *L. lactis*, PAK80 (Israelsen et al., 1995) as described in our co-pending PCT patent application PCT/DK97/00342. The selected plasmid derivatives of pAK80 were pCP34, pCP41 and CP44 (CPX cloning vectors). The atpAGD fragment from pTAC-AGD (from example 1) was first subcloned in a polylinker in order to have the atpAGD fragment flanked by two BamHI sites. Subsequently, this BamHI fragment was cloned into the unique BamHI site downstream of the CP promoters on the plasmids pCP34, pCP41 and CP44, resulting in the plasmids, pCP34::atpAGD, pCP34::2atpAGD, pCP41::atpAGD and CP44::atpAGD, where pCP34::2atpAGD contains two atpAGD fragments in tandem.

Subsequently, the strains were characterized with respect to growth rate, growth yield and glycolytic flux in glucose minimal medium supplemented with 200 μg/ml erythromycin, essentially as described in example 1, see table 2.

The expression of the $F_1$-ATPase subunits had a slightly negative effect on the growth rate as the expresion level increased. The effect on growth yield was much stronger and at the highest expression level the growth yield had dropped to 40% of the initial value. The glycolytic flux was stimulated 70% at the highest expression level of ATPase, and at this expression level the growth rate was lowered by 30%.

TABLE 2

Effect of expression of uncoupled $F_1$-ATPase activity
($E.$ $coli$ α, γ, β subunits) in $E.$ $coli$

| Plasmid | Biomass yield gdw/mmol glucose | Growth rate, μ h−1 | Glucose flux mmol glucose/ h/gdw | Biomass yield % | Growth rate % | Glucose flux % |
|---|---|---|---|---|---|---|
| pCP41 | 0.067 | 0.47 | 6.9 | 100 | 100 | 100 |
| pCP41::atpAGD | 0.047 | 0.42 | 9.1 | 69 | 90 | 131 |
| pCP34 | 0.063 | 0.41 | 6.6 | 100 | 100 | 100 |
| pCP34::atpAGD | 0.034 | 0.34 | 9.9 | 54 | 81 | 149 |
| pCP44 | 0.067 | 0.44 | 6.5 | 100 | 100 | 100 |
| pCP44::atpAGD | 0.027 | 0.30 | 11.2 | 40 | 69 | 172 |

EXAMPLE 3

Expression of $E.$ $coli$ $F_1$-ATPase Activity from Constitutive Promoters in $L.$ $lactis$ The plasmids from example 2 which express the $E.$ $coli$ $F_1$-ATPase subunits to various extent are also capable of replicating in $L.$ $lactis$, and could therefore be used to test whether the $E.$ $coli$ $F_1$-ATPase subunits can be used to hydrolyse ATP in $L.$ $lactis$.

The plasmids pCP34::atpAGD, pCP34::2atpAGD and pCP41::atpAGD, were transformed into the $L.$ $lactis$ subspecies $cremoris$ strain, MG1363, which is used routinely for physiological experiments in this laboratory. In addition we transformed the respective vectors, pCP34 and pCP41 in order to have proper control strains. Subsequently, the resulting transformants were characterized with respect to growth rate, growth yield and glycolytic flux, in comparison to the respective vectors, pCP34 and pCP41, by growing the various cultures in defined medium (SA medium) supplemented with a limiting concentration of glucose (0.1%), see table 3.

TABLE 3

Expression of $E.$ $coli$ $F_1$-ATPase in $L.$ $lactis$

| Plasmid | Biomass yield gdw/mmol glucose | Growth rate, μ h−1 | Glucose flux mmol glucose/ h/gdw | Biomass yield % | Growth rate % | Glucose flux % |
|---|---|---|---|---|---|---|
| pCP34 | 0.073 | 0.664 | 9.161 | 100 | 100 | 100 |
| pCP34::atpAGD | 0.071 | 0.653 | 9.230 | 97.5 | 98.3 | 100.8 |
| pCP34::2atpAGD | 0.069 | 0.655 | 9.560 | 94.6 | 98.7 | 104.4 |
| pCP41 | 0.072 | 0.645 | 8.925 | 100 | 100 | 100 |
| pCP41::atpAGD | 0.070 | 0.590 | 8.461 | 96.5 | 91.5 | 94.8 |

The results show that the plasmids pCP34::atpAGD and pCP34::2atpAGD did affect the growth yield and the glycolytic flux to some extent, but the plasmids were far less efficient in $L.$ $lactis$, compared to $E.$ $coli$. This was probably a consequence of a lower expression of the $E.$ $coli$ ATPase subunits, or some of these, in $L.$ $lactis$, due to a lower copy number of the pAK80 vector in $L.$ $lactis$ (5-10), and due to differences in the translational efficiency of the three individual atp genes which originates from $E.$ $coli$. The plasmid pCP41::atpAGD also resulted in a lower growth yield, indicating that also in this case uncoupled ATP hydrolysis was taking place. However, the pCP41::atpAGD plasmid had a relatively strong inhibitory effect on the growth rate and therefore the glycolytic flux was not increased by this plasmid. It is possible that the heterologous expression of $E.$ $coli$ ATPase subunits resulted in growth inhibition due to effects other than ATP hydrolysis, e.g. by interfering with the function of the $L.$ $lactis$ $F_1F_0$ $H^+$-ATPase complex.

EXAMPLE 4

Expression of $L.$ $lactis$ $F_1$-ATPase Subunits β and ε, in $L.$ $lactis$

In the example above we showed that the expression of $F_1$-ATPase subunits from $E.$ $coli$ in $L.$ $lactis$, resulted in only a small stimulation of the glycolytic flux. It is possible that the heterologous expression of $E.$ $coli$ ATPase subunits resulted in growth inhibition due to effects other than ATP hydrolysis, e.g. by interfering with the function of the $L.$ $lactis$ $F_1F_0$ $H^+$-ATPase complex. In the present example we have expressed the $L.$ $lactis$ $F_1$-ATPase subunits, β and ε, in $L.$ $lactis$, as this appeared to be an effective combination of subunits when expressed in $E.$ $coli$, see example 1. The atpDC$_{Llc}$ genes from $L.$ $lactis$ subspecies $cremoris$ (SEQ ID No. 1) was cloned on a 2.5 kb HindIII fragment into the HindIII restriction site on the standard cloning vector, pBluescript, into $E.$ $coli$ K-12, strain BOE270. Subsequently, the atpDC$_{Llc}$ genes were cut out on a 2.5 kb BamHI-SalI fragment and cloned into 5 expression vectors, pCP32, pCP34, pCP37, pCP41 and pCP44 which had been digested with BamHI and SalI, resulting in the plasmids pCP32::atpDC$_{Llc}$, pCP34::atpDC$_{Llc}$, pCP37::atpDC$_{Llc}$, pCP41::atpDCL$_{lc}$ and pCP44::atpDC$_{Llc}$, respectively, where the lacLM genes downstream of the CP promoters, have been replaced with the atpDC$_{Llc}$ genes. These plasmids should express the $L.$ $lactis$ $F_1$-ATPase subunits, β and ε, to different extent. The plasmids were then transformed into MG1363 with selection for the erythromycin resistance carried by these vectors. Experiments were then performed to test whether the constructs resulted in convertion of ATP into ADP in *L. lactis*. The strains carrying the different constructs was then grown in GM17 medium supplemented with 5 μg/ml erythromycin. The plasmids did not have a strong effect on the growth rate of the cultures, which remained close to the growth rate of the respective vector control plasmids. The yield of biomass, however, decreases for all the cultures by up to 17%, which shows that the cultures did indeed express uncoupled ATPase activity, see table 4.

TABLE 4

Effect of expression of *L. lactis* β and ε subunits on acid production by *L. lactis*, at 30° C. and with initial pH 6.7.

| Plasmid | Biomass* OD$_{450}$ | Final pH* | Acid formation, relative to biomass* % of vector |
|---|---|---|---|
| pCP34 | 5.08 | 4.27 | 100 |
| pCP34::atpDCllc | 4.72 | 4.31 | 98.0 |
| pCP41 | 4.66 | 4.34 | 100 |
| pCP41::atpDCllc | 5.21 | 4.24 | 113.5 |
| pCP37 | 4.89 | 4.28 | 100 |
| pCP37::atpDCllc | 4.63 | 4.24 | 116.1 |
| pCP32 | 4.86 | 4.34 | 100 |
| pCP32::atpDCllc | 3.95 | 4.36 | 116.9 |

Each value is the average of 3-4 independent cultures. The acid production was calculated from the pH change, and normalized by the biomass produced.

The GM17 growth medium used in these experiments contains a surplus of glucose (1%), and growth only stops when the pH of the growth medium becomes lower than approximately pH 4.3. To some extent, this mimics the situation that the lactic acid bacteria experience during cheese and yougurt production. In this medium, the growth yield, in terms of the final cell mass of the cultures, reflects the acid production by these cultures.

In these cultures, the expression of $F_1$-ATPase subunits will increase three fold at approximately OD600 equal to 1.5. This is a consequence of the three fold amplification of the plasmid copy number that has been shown to take place at this point of the growth curve. In reality, the effect of expressing the $F_1$-ATPase subunits may therefore be larger.

To test this hypothesis, we grew some of the strains which expressed the *L. lactis* $F_1$-ATPase subunits β and ε in batch cultures of GM17 medium which had been adjusted to pH 5.9, see Table 5. In addition, the temperature of the growth medium may also affect the plasmid copy number and thus the expression of the $F_1$-ATPase subunits. The experiments were therefore performed at 37° C.

TABLE 5

Effect of expression of *L. lactis* β and ε subunits on acid production by *L. lactis*, at 37° C. and with initial pH 5.9.

| Plasmid | Biomass* OD$_{450}$ | Ffinal pH* | Acid formation, relative to biomass* % of vector |
|---|---|---|---|
| pCP34 | 1.24 | 4.95 | 100 |
| pCP34::atpDC$_{llc}$ | 1.06 | 4.87 | 141.4 |
| pCP37 | 1.00 | 4.96 | 100 |
| pCP37::atpDC$_{llc}$ | 0.58 | 4.92 | 188.4 |

Clearly, the effect of the $F_1$-ATPase activity was much stronger under these growth conditions: the amount of acid produced was almost doubled for the strain carrying the plasmid pCP37::atpDC$_{11c}$.

EXAMPLE 5

Expression of the $F_1$-ATPase Subunits, α, γ, and β, from *L. lactis* Subspecies *cremoris* in *L. lactis* Subspecies *cremoris*

In example 4, only the *L. lactis* $F_1$-ATPase β and ε subunits were expressed in *L. lactis*. However, from the experiments with *E. coli* (example 1), we know that the simultaneous expression of subunits α, γ, and β, is a more powerful combination, which could also be the case for *L. lactis*. In order to obtain the same strong stimulation of the glycolytic flux and acid production in *L. lactis*, a set of vectors similar to the vectors described in example 4 was constructed, in which the atpAGD$_{Llc}$ genes derived from *L. lactis*, encoding the subunits α, γ, and β (SEQ ID No. 1) was expressed from CP promoters with different activities. The atpAGD$_{Llc}$ genes from *L. lactis* was cloned on a 2.5 kb BamHI-SalI fragment into the 5 vectors, pCP32, pCP34, pCP37, pCP41 and pCP44, resulting in the plasmids, pCP32::atpAGD$_{Llc}$, pCP34::atpAGD$_{Llc}$, pCP37::atpAGD$_{Llc}$, pCP41::atpAGD$_{Llc}$, pCP44::atpAGD$_{Llc}$, respectively, where the lacLM genes downstream of the CP promoters, has been replaced with the atpAGD$_{Llc}$ genes. These plasmids will express the *L. lactis* $F_1$-ATPase subunits α, γ, and β, to different extent. The plasmids were transformed into MG1363 with selection for the Erythromycin resistance carried by these vectors. Experiments were then performed to show that the constructs were effective in ATP hydrolysis in *L. lactis* and to what extent the glycolytic flux was enhanced, by growing the five different constructs in GM17 medium supplemented with erythromycin, and measuring the growth rate, ATP and ADP concentrations, the yield of biomass and the rate of acid production.

EXAMPLE 6

Expression of $F_1$-ATPase Subunits from *L. lactis* subsp *lactis*, in *L. lactis* subspecies *lactis*

In the examples 3-5 above, we used the strain *L. lactis* subsp. *cremoris*, MG1363. This strain is plasmid-free and is used routinely in our laboratory as a simple model organism for our physiological studies. But strains belonging to the subspecies *lactis* are also important in cheese production. We therefore cloned and sequenced the at-pAGD$_{Lll}$ genes from *L. lactis* subsp. *lactis*, (SEQ ID No. 6). Subsequently, a 4.2 kb fragment habouring the at-pAGD$_{Lll}$ genes was cloned into 5 vectors, pCP32, pCP34, pCP37, pCP41 and pCP44, resulting in the plasmids, pCP32::atpAGD$_{Lll}$, pCP34::atpAGD$_{Lll}$, pCP37::atpAGD$_{Lll}$, pCP41::atpAG$_{Lll}$, pCP44::atpAGD$_{Lll}$, respectively. These plasmids were then transformed into *L. lactis* subsp. *lactis* as described in example 3. The resulting strains with different expression levels of the $F_1$-ATPase subunits α, γ and β were then used to characterize the effect hereof on the growth yield, growth rate, glycolytic flux, and the cellular energy state of *L. lactis* subsp. *lactis*, as described in the examples 1-5.

EXAMPLE 7

Expression of F1-ATPase Subunits from *S. thermophilus*, ST3, in *S. thermophilus*, ST3

In the examples 3-6 above, we used strains of the genus *Lactococcus*. These strains are important in cheese production. As starter cultures for yougurt production, the dairy industry often uses strains of *S. thermophilus*. We therefore cloned and sequenced the atpAGD$_{St}$ genes from *S. thermophilus*, strain ST3 (SEQ ID No. 10). Subsequently, a 4.2 kb fragment habouring the atpAGD$_{St}$ genes was cloned into the 5 vectors, pCP32, pCP34, pCP37, pCP41 and pCP44, resulting in the plasmids, pCP32::atpAGD$_{St}$, pCP34::atpAGD$_{St}$, pCP37::atpAGD$_{St}$, pCP41::atpAGD$_{St}$, pCP44::atpAGD$_{St}$, respectively. These plasmids were then transformed into *S. thermophilus* strain ST3. The resulting strains have different expression levels of the F$_1$-ATPase subunits α, γ, and β, and were then used to characterize the effect hereof on the growth yield, growth rate, glycolytic flux, and the cellular energy state of *S. thermophilus*, as described in the previous examples.

EXAMPLE 8

Expression of a Truncated F$_1$-ATPase β subunit from *Phaffia rhodozyma* in *Saccharomyces cerevisiae*

In this example we show that uncoupled F$_1$-ATPase expression can also be used to hydrolyze ATP in yeast cells of *Saccharomyces cerevisiae*.

A cDNA gene library was prepared from total RNA, isolated from *Phaffia rhodozyma*, by cloning the cDNA fragments into the expression vector, pYES2.0. One of the resulting plasmids, pATPbeta, gave rise to an ade$^+$ phenotype in the *Saccharomyces cerevisiae* strain, W301, which carries a mutation in the ADE2 gene. Sequencing of the clone revealed a 0.9 kb insert, which encoded a protein of 254 amino acids (SEQ ID No. 14). The encoded protein had a very high homology to the C-terminal part of F$_1$-ATPase β subunits from other organisms, prokaryotic as well as eukaryotic, including the β subunit from *S. cerevisiae* (86% identity).

The ADE2 mutation results in starvation for an intermediate further down in the purine metabolism, AICAR (which under normal conditions is produced by ADE3, two steps further down in this pathway). AICAR is essential for de novo biosynthesis of AMP and GMP, and ADE2 mutants therefore need an alternative purine source in the growth medium. However, there is an alternative route for synthesis of AICAR which involves some of the genes involved in histidine biosynthesis. These genes are normally repressed under the conditions used for the complementation, but when the HIS3 gene is introduced on a plasmid, this complements the ADE2 mutation because the cells start to produce AICAR. Since AICAR is a precursor for ATP, it is likely that a lack of ATP (or increased levels of ADP and AMP) provide a signal to derepress the HIS3 gene and generate AICAR (which will subsequently end up as ATP). Indeed, cross-pathway regulation between purine and histidine biosynthesis has been found in yeast and involves the transcription factors BAS1 and BAS2. A reasonable explanation for the ade$^+$ phenotype conferred by the plasmid, is therefore that the plasmid gives rise to ATP hydrolysis in the cytoplasm, thereby effecting the concentrations of adenine nucleotides in the cytoplasm.

Importantly, this truncated β subunit from *Phaffia rhodozyma* that was encoded on pATPbeta, included the region of the β subunit which is thought to encode the catalytic site for ATP hydrolysis. The truncation of the N-terminal part of the β subunit probably means that the protein will no longer be exported into the mitochondrion, but should stay within the yeast cytoplasm.

The truncated β subunit pATPbeta is expressed from a gal promoter, i.e. it can be induced with galactose. If the truncated β subunit encoded by the clone is active in ATP hydrolysis it should result in a decrease in the growth yield, and at sufficiently high expression level, we should also observe inhibition of growth. The strain which expressed the truncated β subunit and a control strain (which contained a plasmid pHIS3 containing a HIS3 gene from *Phaffia rhodozyma*), were streaked on plates containing galactose as the energy source, which will give maximal expression of the truncated β subunit. Indeed, the growth of the strain which expressed the truncated β subunit was strongly inhibited by the presence of galactose, whereas the control strain grew normally. As a control, the growth of the two strains were also compared on a plate containing glucose as the energy source, conditions under which the expression of the β subunit should be repressed, and indeed we observed little difference in growth of the two strains on these plates, see table 6.

Subsequently, for the purpose of the physiological investigations, the two strains were converted into Rho$^-$ strains (petit mutants, defective in oxidative phosphorylation) by standard treatment with ethidium bromide. The induction with galactose caused even stronger inhibition of growth in the Rho$^-$ background, which further indicates that the cause of the growth inhibition is uncoupled ATP hydrolysis in the cytoplasm.

TABLE 6

Effect of expression of a truncated F$_1$-ATPase β subunit from *Phaffia rhodozyma* in *S. cerevisiae* on SC plates

| Strain/plasmid | SC-ura + glucose | SC-ura + galactose |
|---|---|---|
| Rho$^+$/pATPbeta | +++++ | + |
| Rho$^+$/pHIS3 | ++++ | +++ |
| Rho$^-$/pATPbeta | +++++ | – |
| Rho$^-$/pHIS3 | ++++ | +++ |

Growth experiments were performed to measure the resulting changes in the ATP/ADP ratio and the degree of stimulation of the glycolytic flux and ethanol formation, essentially as described in the examples above, and to show that the truncated β subunit from *Phaffia rhodozyma* is active with respect to converting ATP into ADP in the yeast cell.

EXAMPLE 9

Expression of F$_1$-ATPase β subunit from *Trichoderma reesei* in *Saccharomyces cerevisiae*

In this example we show that the expression of the F$_1$-ATPase β subunit from the filamentous fungus, *Trichoderma reesei* can be used to improve the product formation of *Saccharomyces cerevisiae*.

The gene encoding the F$_1$-ATPase β subunit homologue from *Trichoderma reesei* was isolated from a cDNA library, inserted into a multicopy expression vector, pAJ401. DNA sequencing (SEQ ID 16) revealed that the cloned gene had very high homology to the β subunits from *Neurospora crassa* (91% identity), *Kluyveromyces lactis* (68%) and *Saccharomyces cerevisiae* (68%). Importantly, the first 43 amino acids in this β subunit, which encodes the signal for exporting the protein into the mitochondria, was homologous to the N-terminal part of the β subunit from *Neurospora crassa* (58% identity), but not to that of Saccharomyces cerevisiae. It is therefore likely that the β subunit from *Trichoderma reesei* will stay within the cytoplasm when expressed in *Saccharomyces cerevisiae*. This is important for the many cases where the fermentation is carried out anaerobically, because in these cases it is probably most efficient if the ATP hydrolysis takes place in the cytoplasm. Alternatively, in those cases where the β subunit is transported into the mitochondrion, it may be useful to genetically modify the β subunit so that is stays within the cytoplasm.

The gene encoding the $F_1$-ATPase β subunit homologue from *Trichoderma reesei* was expressed in *S. cerevisiae* strain VW1b (MAT alpha, leu2-3/112, ura3-52, trp1-289, his3D1, MAL2-8c, SUC2). To test whether the presence of the *T. reesei* β subunit resulted in ATP hydrolysis in the cytoplasm of the *Saccharomyces cerevisiae* host cells, we measured the intracellular concentrations of ATP, ADP and AMP, under various growth conditions in cultures of two strains expressing the β subunit (pATPβ34 and pATPβ44) and a strain carrying the vector plasmid, pFL60, see table 7.

TABLE 7

Effect of expression of *T. reesei* β subunit on ATP, ADP and AMP concentrations in *S. cerevisiae*

| Strain | ATP μmol/gdw | ADP μmol/gdw | AMP μmol/gdw | ATP/ADP ratio |
|---|---|---|---|---|
| Aerobic/exp.phase | | | | |
| pATPβ34 | 19.3 | 5.58 | 3.31 | 3.5 |
| pATPβ44 | 13.9 | 5.15 | 3.25 | 2.7 |
| pVECTOR | 16.6 | 5.47 | 3.43 | 3.0 |
| Aerobic/stat.phase | | | | |
| pATPβ34 | 9.30 | 4.03 | 2.89 | 2.3 |
| pATPβ44 | 8.99 | 3.90 | 2.42 | 2.3 |
| pVECTOR | 19.5 | 4.62 | 2.87 | 4.2 |
| anaerobic/stat.phase | | | | |
| pATPβ34 | 4.39 | 11.6 | 6.72 | 0.4 |
| pATPβ44 | 3.14 | 10.5 | 6.65 | 0.3 |
| pVECTOR | 8.84 | 10.2 | 6.37 | 0.9 |

* according to Bergmeyer (1985)

The β subunit did not appear to have a significant effect on the concentrations of ATP, ADP and AMP in cells growing on glucose in the exponential growth phase. The reason is probably that the ATP concentration that the homeostatic control of ATP synthesis can here keep up with the extra drain on ATP conferred by the β subunit $F_1$-ATPase activity. Indeed, the growth rate of these cultures was unaffected by the presence of the $F_1$-ATPase activity, see table 7. But in the stationary cultures the concentration of ATP decreased significantly in the cultures expressing the β subunit, compared to the control. The effect was strongest in the anaerobically grown cultures where the ATP was lowered by a factor of 2-3. In these cultures, ATP must be generated through oxidative phosphorylation, (which is not even an option for the anaerobic cultures), and any effect of uncoupled ATP hydrolysis should therefore indeed be stronger in these cells.

Shake Flask Cultivations of Cultures Expressing the $F_1$-ATPase β Subunit Homologue in *Saccharomyces cerevisiae*.

Shake flask cultivations were performed under microaerobic/anaerobic conditions with volume ratio 1/1.25 and no agitation; with 400 ml growth media in 500 ml Erlenmeyers on magnetic stirring. The growth media contained 5 g/l of glucose and amino acids and bases according to synthetic complete medium (SC-ura+0.5% G). $OD_{600}$ was monitored during the cultivation (OD600=1.0 is equal to 0.3 g/l dry weight). Ethanol and glucose were measured with HPLC (Waters, Sugar-Pak or IC-Pak columns). Production of ethanol (grams of ethanol per grams of cell dry weight) is shown in Table 8.

TABLE 8

Effect of expression of *T. reesei* β subunit, on fluxes of ethanol and glucose in *s. cerevisiae*

| Strain | μ h$^{-1}$ | $J_{gluc}$ g/h/gdw | $J_{etoh}$ g/h/gdw | $J_{gluc}$ relative to control | $J_{etoh}$ relative to control |
|---|---|---|---|---|---|
| pATPβ34 | 0.40 | 2.811 | 1.190 | 107.7 | 105.6 |
| pATPβ44 | 0.40 | 2.750 | 1.187 | 105.3 | 105.3 |
| pVECTOR control | 0.39 | 2.611 | 1.127 | 100 | 100 |

These data show that the presence of the *T. reesei* $F_1$-ATPase β subunit resulted in an increased flux of glucose, as well as ethanol, in the *Saccharomyces cerevisiae* host cells.

REFERENCES

Casabadan, M. J., and Cohen, S. N. (1980). *J. Mol. Biol.*, 138, 179-207.

Israelsen, H. (1995). Cloning and partial characterization of regulated promoters from *Lactococcus lactis* Tn917-lacZ integrants with the new promoter probe vector, pAK80. *Appl. Environ. Microbiol.*, 61, 2540-2547.

Maniatis, T., Fritsch, E. F., and Sambrook, J., (1982). *Molecular cloning*. Cold Spring Harbor Laboratory Press, Cold Spring Harbor, N.Y.

Miller, J. H., (1972). *Experiments in molecular genetics*, Cold Spring Harbor Laboratory Press, Cold Spring Harbor, N.Y.

Starck, M. J. R. (1987). Multicopy expression vectors carrying the lac repressor gene for regulated high-level expression of genes in *Escherichia coli*. *Gene* 51, 255-267.

von Meyenburg, K., Joergensen, B. B., and van Deurs, B. (1984). Physiological and morphological effects of overproduction of membrane-bound ATP synthase in *Escherichia coli* K-12. *EMBO J.* 3, 1791-1797.

Yanisch-Perron, C., Vieira, J., and Messing, J. (1985). Improved M13 phage cloning vectors and host strains: nucleotide sequences of the M13mp18 and pUC19 vectors. *Gene* 33, 103-109.

The invention claimed is:

1. A method of increasing the conversion rate of a sugar substrate by a cell or decreasing the production of biomass, said method comprising the steps of:
  (i) expressing an uncoupled ATPase activity in said cell resulting in inducing the conversion of ATP to ADP without primary effects on other cellular metabolites or functions, and
  (ii) incubating the cell with a suitable sugar substrate to achieve an increased conversion rate of said sugar or decreased production of biomass relative to the amount of sugar converted or biomass produced by a cell not expressing said uncoupled ATPase activity.

2. A method according to claim 1, characterized by expressing in said cell the soluble part ($F_1$) of the membrane bound ($F_0F_1$ type) $H^+$-ATPase or a portion of $F_1$ exhibiting ATPase activity.

3. A method according to claim 1, wherein said cell is a prokaryotic cell.

4. A method according to claim 3, wherein said cell is selected from the group consisting of bacteria belonging to the genera *Lactococcus, Streptococcus, Enterococcus, Lactobacillus, Leuconostoc, Escherichia, Zymomonas, Bacillus* and *Pseudamonas*.

5. A method according to claim 1, wherein said cell is a eukaryotic cell.

6. A method according to claim 5, wherein said cell is a yeast cell.

7. A method according to claim 6, wherein said cell belongs to *Saccharomyces cerevisiae* or *Trichoderma reesei*.

8. A method according to claim 1, wherein said cell is transformed or transfected with an expression vector including DNA encoding $F_1$ or a portion thereof exhibiting ATPase activity under the control of a promoter functioning in said cell, and said DNA is expresses in the cell.

9. A method according to claim 8, wherein said DNA encoding $F_1$ or a portion thereof is homologous to said cell.

10. A method according to claim 8, wherein said DNA encoding $F_1$ or a portion thereof is heterologous to said cell.

11. A method according to claim 8, wherein said DNA encoding F.sub.1 or a portion thereof is derived from a prokaryotic organism.

12. A method according to claim 11, wherein said DNA encoding $F_1$ or a portion thereof is derived from *Escherichia coli, Lactococcus lactis* or *Streptococcus thermophilus* and is selected from the group consisting of the gene encoding the $F_1$ subunit β or a portion thereof and various combinations of said gene or portion with the genes encoding the $F_1$ subunits δ, α, γ and ε or portions thereof.

13. A method according to claim 12, wherein said DNA encoding $F_1$ or a portion thereof is selected from the group consisting of the *Escherichia coli, Streptococcus thermophilus* and *Lactococcus lactis* genes atpHAGDC (coding for subunits δ, α, γ, β, ε), atpAGDC (coding for subunits α, γ, β, ε), atpAGD (coding for subunits α, γ, β, ε), atpDC (coding for subunits β, ε) and atpD (coding for subunit β alone).

14. A method according to claim 8, wherein said DNA encoding F.sub.1 or a portion thereof is derived from a eukaryotic organism.

15. A method according to claim 14, wherein said DNA encoding $F_1$ or a portion thereof is derived from *Saccharomyces cerevisiae, Phaffia rhodozyma* or *Trichoderma reesei* and is selected from the group consisting of the gene encoding the $F_1$ subunit β or a portion thereof and various combinations of said gene or portion with the genes encoding the other $F_1$ subunits or portions thereof.

* * * * *